United States Patent
Jin et al.

(10) Patent No.: US 11,225,460 B2
(45) Date of Patent: Jan. 18, 2022

(54) PYRROLIDINEAMIDE DERIVATIVES AND USES THEREOF

(71) Applicant: SUNSHINE LAKE PHARMA CO., LTD., Guangdong (CN)

(72) Inventors: Chuanfei Jin, Dongguan (CN); Kangzhi Chen, Dongguan (CN); Yingjun Zhang, Dongguan (CN)

(73) Assignee: SUNSHINE LAKE PHARMA CO., LTD., Dongguan (CN)

( * ) Notice: Subject to any disclaimer, the term of this patent is extended or adjusted under 35 U.S.C. 154(b) by 4 days.

(21) Appl. No.: 16/977,487

(22) PCT Filed: Mar. 7, 2019

(86) PCT No.: PCT/CN2019/077249
§ 371 (c)(1),
(2) Date: Sep. 2, 2020

(87) PCT Pub. No.: WO2019/170115
PCT Pub. Date: Sep. 12, 2019

(65) Prior Publication Data
US 2021/0053918 A1 Feb. 25, 2021

(51) Int. Cl.
*C07D 207/09* (2006.01)

(52) U.S. Cl.
CPC .................. *C07D 207/09* (2013.01)

(58) Field of Classification Search
CPC .................................................. C07D 207/09
See application file for complete search history.

(56) References Cited

U.S. PATENT DOCUMENTS

| | | |
|---|---|---|
| 5,236,957 A | 8/1993 | Dostert et al. |
| 7,037,935 B2 | 5/2006 | Iding et al. |
| 7,456,210 B2 | 11/2008 | Rodriguez-Sarmiento et al. |
| 7,501,528 B2 | 3/2009 | Hildbrand et al. |
| 8,445,539 B2 | 5/2013 | Izzo et al. |
| 2007/0078172 A1 | 4/2007 | McElroy et al. |
| 2020/0039930 A1 | 2/2020 | Backfisch et al. |

FOREIGN PATENT DOCUMENTS

| | | | |
|---|---|---|---|
| CN | 101559053 A | | 10/2009 |
| EP | 1 524 265 | * | 4/2005 |
| WO | 2000/033788 A2 | | 6/2000 |
| WO | 2005/040108 A1 | | 5/2005 |
| WO | 2014/053210 A1 | | 4/2014 |

OTHER PUBLICATIONS

Hobson D. Adrian et al., "Discovery of A-971432, An Orally Bioavailable Selective Sphingosine-1-Phosphate Receptor 5 (S1p5) Agonist for the Potential Treatment of Neurodegenerative Disorders" Journal of Medicinal Chemistry, vol. 58, pp. 9154-9170, 2015.
May 29, 2019 International Search Report issued in Internaitonal Patent Application No. PCT/CN2019/077249.
May 29, 2019 Written Opinion issued in International Patent Application No. PCT/CN2019/077249.

* cited by examiner

*Primary Examiner* — Timothy R Rozof
(74) *Attorney, Agent, or Firm* — Oliff PLC

(57) ABSTRACT

A pyrrolidineamide derivatives and uses thereof, specifically, the present invention relates to a novel pyrrolidineamide compound and a pharmaceutical composition containing this compound, which can be used as a MAO-B inhibitor. The present invention also relates to methods of preparing this compound and pharmaceutical composition, and their use in the manufacture of a medicament for treating a disease regulated by MAO-B comprising a neurodegenerative disease, especially Parkinson's disease.

18 Claims, No Drawings

PYRROLIDINEAMIDE DERIVATIVES AND USES THEREOF

CROSS-REFERENCE TO RELATED APPLICATIONS

This application claims priority to Chinese Patent Application Serial No 201810192198.6, filed on Mar. 8, 2018, which is hereby incorporated by reference in its entirety.

FIELD OF THE INVENTION

The invention pertains to the pharmaceutical field, and it relates to compounds used for treating Parkinson's disease, and to pharmaceutical compositions containing these compounds and their usage methods and uses. In particular, these compounds of the invention are pyrrolidineamide derivatives used as MAO-B inhibitors.

BACKGROUND OF THE INVENTION

Parkinson's disease (PD) is a common chronic degenerative disease of nervous system, it is common in elderly, the average age of onset is about 60 years old, and Parkinson's disease is rare in young people under 40 years old. The prevalence of PD among people over 65 years old in China is about 1.7%. Most patients with Parkinson's disease are sporadic cases, and fewer than 10% of them have the family history. Parkinson's disease has an insidious onset and the progress is slow. Usually, the initial symptom is tremor or clumsiness in the limbs of one side, then which affects the limbs of the other side. The main clinical manifestations are static tremor, bradykinesia, muscle rigidity and postural gait disorder. In recent years, more and more people have noticed that non-motor symptoms such as depression, constipation and sleep disorder and so on are also common chief complaints of Parkinson patients, and the non-motor symptoms influence on the quality of life of patients is even greater than motor symptoms.

The main pathological change of Parkinson's disease is degenerative death of dopamine (DA) neurons in the substantia nigra of the midbrain, which results in a significant decrease in DA content in the striatum and then leads to disease. The exact cause of this pathological change is still not known. Genetic factors, environmental factors, aging, oxidative stress and so on all may play a role in the process of degenerative death of PD dopaminergic neurons.

Most cases of illness may be related to environmental factors or the interaction between environmental factors and genetic factors. Part of the pathogenesis involves free radicals, oxidative stress, glutamate excitotoxicity, lack of neurotrophic agents, inflammation, apoptosis and mitochondrial complex I deletion. Interaction of these mechanisms in cascade biochemical reactions eventually leads to neuronal death. (Teismann P, Schulz J B. Cellular pathology of Parkinson's disease: astrocytes, microglia and inflammation [J]. Cell Tissue Res, 2004, 318: 149-161). Genetic factors play a decisive role in some familial PD. Recent genetic studies have found that ubiquitin-proteasome system dysfunction and abnormal aggregation of denatured proteins play important roles in the pathogenesis of most PD. In addition, some factors such as oxidative stress, the formation of free radicals, glutamate over-release-mediated excitotoxicity, mitochondrial dysfunction, inflammation and neuronal apoptosis caused by ubiquitin-proteasome system damage and so on are closely related to the progress of the disease.

At present, the main treatment of PD is the symptomatic treatment of dopamine substitution. L-dopa is still the most effective drug to control the signs and symptoms of PD. (RASCO O, GOETZ C, KOLLER W, et al. Treatment interventions for Parkinson's disease: an evidence based assessment [J]. Lancet, 2002, 359 (9317): 1589-1598). Although L-dopa can temporarily improve the PD symptoms, long term treatment with L-dopa can lead to many adverse reactions such as dyskinesia, motor fluctuations and psychiatric symptoms. Although the administration of continuous DA neuron stimulation, deep brain stimuli (DBS) through surgical pathways, and long-acting dopamine receptor agonists can reduce these complications in some extent (SCHAPIRA A H V, EMREB M, JENNER P, et al. Levodopa in the treatment of Parkinson's disease [J]. Eur J Neurol, 2009, 16 (9): 982-989), it can not delay the disease progression. In addition, dopamine receptor agonists such as cabergoline, catechol-oxo-methyltransferase inhibitors (COMT) such as comtan, glutamate receptor antagonists such as memantine, and anticholinergic agents such as Benzhexol (Artane) all produce adverse reactions, but they can be used as adjuvant drugs for levodopa, and enhance the efficacy of levodopa through different mechanisms of drug combinations, reduce the dosage of levodopa and reduce adverse reactions. Therefore, it is particularly important to develop novel drugs that can not only improve the symptoms of DA and non-DA systems in patients with PD, but also slow down or even prevent the disease progression and play a neuroprotective role.

Monoamine oxidase (MAO, EC 1.4. 3.4) is a flavin-containing enzyme responsible for the oxidative deamination of endogenous monoamine neurotransmitters such as dopamine, serotonin, adrenaline, or noradrenaline, and trace amines, e.g. phenylethyl-amine, as well as a number of amine xenobiotics. The enzymes are divided into two forms, monoamine oxidase A (MAO-A) and monoamine oxidase B (MAO-B). They are encoded by different genes (A. W. Bach et al., Proc. Natl. Acad. Sci USA 1988, 85, 4934-4938) and differ in tissue distribution, structure and substrate specificity. MAO-A mainly exists in the liver, gastrointestinal mucosa, it can inactivate catecholamines in the blood circulation system and vasoactive substances in the dietary (such as tyrosine), thus assisting the degradation of neurotransmitters in the brain; and MAO-B mainly exists in the brain and platelets. MAO-A has higher affinity with octopamine, serotonin, adrenaline and noradrenaline; whereas the natural substrates for MAO-B are tyramine and phenylethylamine. And both isoforms can oxidize dopamine.

Monoamine oxidase B (MAO-B) is one of the key enzymes in DA catabolism. It can prolong the action time of dopamine by selectively and specifically inhibiting endogenous and exogenous dopamine decomposition, thus improving clinical symptoms. MAO-B can be used in early monotherapy of PD and adjunctive therapy after motor fluctuations. There are three main functions: (1) decomposition of dopamine into 3,4-dihydroxyphenylacetic acid and homovanillic acid, producing small molecule $H_2O_2$ having toxic effects on nerve cells; (2) deactivation of beta-phenylethylamine that stimulates dopamine secretion and inhibits dopamine re-uptake by deamination; (3) decomposition of 1-methyl-4-phenyl-1,2,3,6-tetrahydropyridine (MPTP) into 1-methyl-4-phenylpyridine ion (MPP+) having neurotoxic. Therefore, according to the physiological function of MAO-B, on the one hand, inhibition of the activity of MAO-B can reduce the degradation and re-uptake of dopamine, thus increase of the concentration of dopamine in brain can improve the clinical symptoms of PD; on the other hand, reducing the levels of neurotoxins such as hydrogen peroxide and MPP+ to delay the death process of substantia nigra (HEIKKILA R E, MANZINO L, CABBAT F S, et al. Protection against the dopaminergic neurotoxiciy of 1-methyl-1,2,3,6-tetrahydropyridine (MPTP) by monoamine inhibitors [P]. Nature, 1984, 311 (5985): 467-469; YOUDIM M B H, BAKHLE Y S. Monoamine oxidase isoforms and inhibitors in Parkinson's disease and depressive illness [J]. Br J Pharmacol, 2006, 147 (S1): S287-S296; NAOI M, WAKAKO M. Monoamine oxidase inhibitors as neuroprotective agents in age-dependent neurodegenerative disorders [J]. Curr Pharm Des, 2010, 16 (25): 2799-2817), can change the PD process. MAO-B inhibitor can not only improve the symptoms of PD, but also play a neuroprotective role, so it is a hot topic in the drug research of anti-Parkinson's disease at present.

Some studies on MAO-B inhibitors have been carried out now:

Prolinamide derivatives as Na/Ca channel blockers or selective MAO-B inhibitors were disclosed in WO 2005040108 A1, which can treat many diseases, including neurological diseases, cardiovascular diseases, inflammatory diseases, ophthalmological diseases, urinary system diseases, metabolic diseases and gastrointestinal diseases.

α-Aminoamide derivatives with a variety of mechanisms (including NMDA antagonism, MAO-B inhibition, glutamate release, DA reuptake inhibition and Na/Ca channel blocking) were disclosed in WO 2009080470 A1 used for the treatment of schizophrenia, anxiety disorders and Parkinson's disease.

Benzyloxy derivatives were disclosed in WO 2006013049 A2 as MAO-B inhibitors used for the treatment of acute and chronic nervous system diseases, cognitive impairments and memory deficits (including Parkinson's disease), especially Alzheimer's disease and senile dementia.

4-Pyrrolidone-phenyl-benzyl ether derivatives were disclosed in WO 2004026826A1 as MAO-B inhibitors used for the treatment of acute and chronic nervous system diseases, cognitive impairments and memory deficits (including Parkinson's disease), especially Alzheimer's disease and senile dementia.

α-Aminoamide derivatives as MAO-B inhibitors were disclosed in WO 2016052928 A1, which have excellent stability and better efficacy compared with traditional reversible MAO-B inhibitors. They were used for the treatment of neurodegenerative diseases.

Substituted aryl-cyclopropylamine acetamide compounds and substituted heteroaryl-cyclopropylamine acetamide compounds were disclosed in WO 2011042217 A1 as selective LSD1/MAO-B inhibitors used for the treatment of cancer and neurodegenerative diseases.

Fluorobenzamide derivatives were disclosed in WO 2003106380 A2 as selective MAO-B inhibitors used for the treatment of Alzheimer's disease and senile dementia.

Pyridylamide derivatives were disclosed in WO 2003066596 A1 as selective MAO-B inhibitors used for the treatment of neurological diseases, including Alzheimer's disease, senile dementia, Parkinson's disease and depression.

However, further studies are needed in order to find more and better, effective MAO-B inhibitors.

SUMMARY OF THE INVENTION

The invention provides a novel pyrrolidine amide derivative used as a MAO-B inhibitor, and which has good inhibitory effect on the activity of MAO-B. Therefore, it can be used to treat neurodegenerative diseases, especially Parkinson's disease. It can also be used in the manufacture of a medicament for treating neurodegenerative diseases, especially Parkinson's disease. The experimental results show that the pyrrolidineamide derivatives have stable properties, good safety, favorable pharmacodynamic characteristics and good pharmacokinetic properties, such as good brain/plasma ratio, good bioavailability or good metabolic stability, and so on. Therefore, it has a good clinical application prospect.

The invention also provides a method for preparing the compound and a pharmaceutical composition containing the compound, and uses of the compound and the pharmaceutical composition in the manufacture of a medicament.

In one aspect, provided herein is a compound having Formula (I) or a stereoisomer, a geometric isomer, a tautomer, an N-oxide, a hydrate, a solvate, a metabolite, a pharmaceutically acceptable salt or a prodrug thereof,

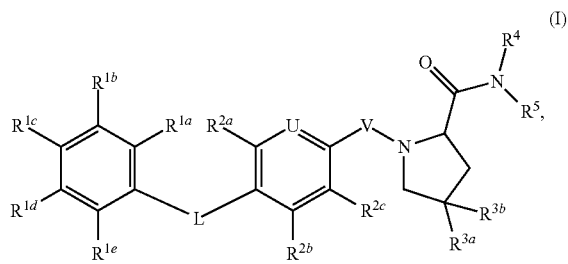

wherein
L is —CH$_2$O— or —OCH$_2$—;
U is CR$^u$ or N;
V is —CH$_2$—, —CH$_2$CH$_2$— or a single bond;
each R$^{1a}$, R$^{1b}$, R$^{1c}$, R$^{1d}$ and R$^{1e}$ is independently H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—(C$_1$-C$_6$ alkyl), —C(=O)—(C$_1$-C$_6$ alkoxy), C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ haloalkoxy, C$_1$-C$_6$ alkylthio, C$_1$-C$_6$ alkylamino, hydroxy-substituted C$_1$-C$_6$ alkyl, C$_3$-C$_8$ cycloalkyl, 3-8 membered heterocyclyl, C$_6$-C$_{10}$ aryl or 5-10 membered heteroaryl;

R$^u$ is H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—(C$_1$-C$_6$ alkyl), —C(=O)—(C$_1$-C$_6$ alkoxy), C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ haloalkoxy, C$_1$-C$_6$ alkylthio, C$_1$-C$_6$ alkylamino, hydroxy-substituted C$_1$-C$_6$ alkyl, C$_3$-C$_8$ cycloalkyl, 3-8 membered heterocyclyl, C$_6$-C$_{10}$ aryl or 5-10 membered heteroaryl;

each R$^{2a}$, R$^{2b}$ and R$^{2c}$ is independently H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—(C$_1$-C$_6$ alkyl), —C(=O)—(C$_1$-C$_6$ alkoxy), C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ haloalkoxy, C$_1$-C$_6$ alkylthio, C$_1$-C$_6$ alkylamino, hydroxy-substituted C$_1$-C$_6$ alkyl, C$_3$-C$_8$ cycloalkyl, 3-8 membered heterocyclyl, C$_6$-C$_{10}$ aryl or 5-10 membered heteroaryl;

R$^{3a}$ is D, F, Cl, Br, I, C$_1$-C$_6$ alkyl, C$_1$-C$_6$ haloalkyl, C$_2$-C$_6$ alkoxy, C$_1$-C$_6$ haloalkoxy or hydroxy-substituted C$_1$-C$_6$ alkyl;

R$^{3b}$ is H, D, F, Cl, Br, I, C$_1$-C$_6$ alkyl, C$_1$-C$_6$ haloalkyl, C$_1$-C$_6$ alkoxy, C$_1$-C$_6$ haloalkoxy or hydroxy-substituted C$_1$-C$_6$ alkyl; and each $R^4$ and $R^5$ is independently H, D, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylamino, hydroxy-substituted $C_1$-$C_6$ alkyl, $C_3$-$C_8$ cycloalkyl, 3-8 membered heterocyclyl, $C_6$-$C_{10}$ aryl or 5-10 membered heteroaryl, wherein each of the $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylamino, hydroxy-substituted $C_1$-$C_6$ alkyl, $C_3$-$C_8$ cycloalkyl, 3-8 membered heterocyclyl, $C_6$-$C_{10}$ aryl and 5-10 membered heteroaryl is independently and optionally substituted with 1, 2, 3, 4 or 5 substituents selected from D, F, Cl, Br, I, —OH, —NH$_2$, —NO$_2$, —CN, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl or $C_6$-$C_{10}$ aryl.

In some embodiments, each $R^{1a}$, $R^{1b}$, $R^{1c}$, $R^{1d}$ and $R^{1e}$ is independently H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—($C_1$-$C_4$ alkyl), —C(=O)—($C_1$-$C_4$ alkoxy), $C_1$-$C_4$ alkyl, $C_2$-$C_4$ alkenyl, $C_2$-$C_4$ alkynyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ alkylamino, hydroxy-substituted $C_1$-$C_4$ alkyl, $C_3$-$C_6$ cycloalkyl, 3-6 membered heterocyclyl, $C_6$-$C_{10}$ aryl or 5-10 membered heteroaryl;

$R^u$ is H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—($C_1$-$C_4$ alkyl), —C(=O)—($C_1$-$C_4$ alkoxy), $C_1$-$C_4$ alkyl, $C_2$-$C_4$ alkenyl, $C_2$-$C_4$ alkynyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ alkylamino, hydroxy-substituted $C_1$-$C_4$ alkyl, $C_3$-$C_6$ cycloalkyl, 3-6 membered heterocyclyl, $C_6$-$C_{10}$ aryl or 5-10 membered heteroaryl;

each $R^{2a}$, $R^{2b}$ and $R^{2c}$ is independently H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—($C_1$-$C_4$ alkyl), —C(=O)—($C_1$-$C_4$ alkoxy), $C_1$-$C_4$ alkyl, $C_2$-$C_4$ alkenyl, $C_2$-$C_4$ alkynyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ alkylamino, hydroxy-substituted $C_1$-$C_4$ alkyl, $C_3$-$C_6$ cycloalkyl, 3-6 membered heterocyclyl, $C_6$-$C_{10}$ aryl or 5-10 membered heteroaryl.

In other embodiments, each $R^{1a}$, $R^{1b}$, $R^{1c}$, $R^{1d}$ and $R^{1e}$ is independently H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—CH$_3$, —C(=O)—OCH$_3$, methyl, ethyl, n-propyl, i-propyl, allyl, propenyl, propargyl, propinyl, —CHF$_2$, —CF$_3$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofiranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl or quinolyl;

$R^u$ is H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—CH$_3$, —C(=O)—OCH$_3$, methyl, ethyl, n-propyl, i-propyl, allyl, propenyl, propargyl, propinyl, —CHF$_2$, —CF$_3$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofuranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl or quinolyl;

each $R^{2a}$, $R^{2b}$ and $R^{2c}$ is independently H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—CH$_3$, —C(=O)—OCH$_3$, methyl, ethyl, n-propyl, i-propyl, allyl, propenyl, propargyl, propinyl, —CHF$_2$, —CF$_3$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofuranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl or quinolyl.

In some embodiments, $R^{3a}$ is D, F, Cl, Br, I, $C_1$-$C_4$ alkyl, $C_1$-$C_4$ haloalkyl, $C_2$-$C_4$ alkoxy, $C_1$-$C_4$ haloalkoxy or hydroxy-substituted $C_1$-$C_4$ alkyl;

$R^{3b}$ is H, D, F, Cl, Br, I, $C_1$-$C_4$ alkyl, $C_1$-$C_4$ haloalkyl, $C_1$-$C_4$ alkoxy, $C_1$-$C_4$ haloalkoxy or hydroxy-substituted $C_1$-$C_4$ alkyl.

In other embodiments, $R^{3a}$ is D, F, Cl, Br, I, methyl, ethyl, n-propyl, i-propyl, —CHF$_2$, —CF$_3$, —CHFCH$_2$F, —CF$_2$CHF$_2$, —CH$_2$CF$_3$, —CH$_2$CF$_2$CHF$_2$, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, hydroxymethyl or 2-hydroxyethyl;

$R^{3b}$ is H, D, F, Cl, Br, I, methyl, ethyl, n-propyl, i-propyl, —CHF$_2$, —CF$_3$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, hydroxymethyl or 2-hydroxyethyl.

In some embodiments, each $R^4$ and $R^5$ is independently H, D, $C_1$-$C_4$ alkyl, $C_2$-$C_4$ alkenyl, $C_2$-$C_4$ alkynyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ alkylamino, hydroxy-substituted $C_1$-$C_4$ alkyl, $C_3$-$C_6$ cycloalkyl, 3-6 membered heterocyclyl, $C_6$-$C_{10}$ aryl or 5-10 membered heteroaryl, wherein each of the $C_1$-$C_4$ alkyl, $C_2$-$C_4$ alkenyl, $C_2$-$C_4$ alkynyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ alkylamino, hydroxy-substituted $C_1$-$C_4$ alkyl, $C_3$-$C_6$ cycloalkyl, 3-6 membered heterocyclyl, $C_6$-$C_{10}$ aryl and 5-10 membered heteroaryl is independently and optionally substituted with 1, 2, 3, 4 or 5 substituents selected from D, F, Cl, Br, I, —OH, —NH$_2$, —NO$_2$, —CN, $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl or $C_6$-$C_{10}$ aryl.

In other embodiments, each $R^4$ and $R^5$ is independently H, D, methyl, ethyl, n-propyl, i-propyl, allyl, propenyl, propargyl, propinyl, —CHF$_2$, —CF$_3$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofuranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl or quinolyl, wherein each of the methyl, ethyl, n-propyl, i-propyl, allyl, propenyl, propargyl, propinyl, —CHF$_2$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCHFCH$_2$F, —OCF$_2$CHF$_2$, —OCH$_2$CF$_3$, —OCH$_2$CF$_2$CHF$_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofuranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl and quinolyl is independently and optionally substituted with 1, 2, 3, 4 or 5 substituents selected from D, F, Cl, Br, I, —OH, —NH$_2$, —NO$_2$, —CN, methyl, ethyl, n-propyl, i-propyl, —CHF$_2$, —CF$_3$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, cyclopropyl, cyclobutyl, cyclopentyl, cyclohexyl, phenyl, indenyl or naphthyl.

In some embodiments, provided herein is a compound having Formula (II) or a stereoisomer, a geometric isomer, a tautomer, an N-oxide, a hydrate, a solvate, a metabolite, a pharmaceutically acceptable salt or a prodrug thereof,

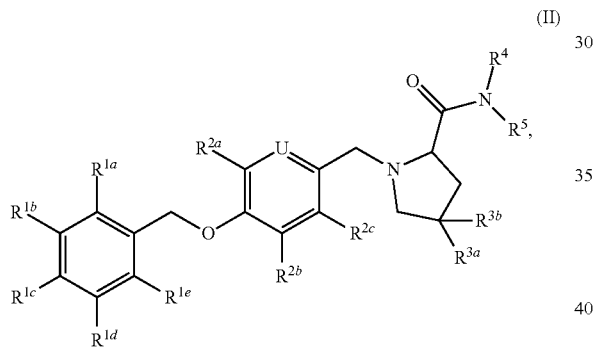

(II)

wherein each $R^{1a}$, $R^{1b}$, $R^{1c}$, $R^{1d}$, $R^{1e}$, $R^{2a}$, $R^{2b}$, $R^{2c}$, $R^{3a}$, $R^{3b}$, $R^4$, $R^5$ and U is as defined herein.

In other embodiments, provided herein is a compound having Formula (III) or a stereoisomer, a geometric isomer, a tautomer, an N-oxide, a hydrate, a solvate, a metabolite, a pharmaceutically acceptable salt or a prodrug thereof,

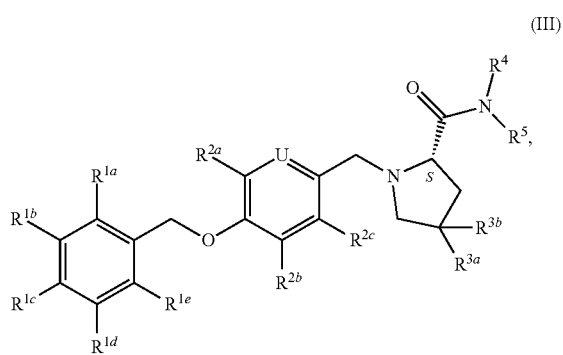

(III)

wherein each $R^{1a}$, $R^{1b}$, $R^{1c}$, $R^{1d}$, $R^{1e}$, $R^{2a}$, $R^{2b}$, $R^{2c}$, $R^{3a}$, $R^{3b}$, $R^4$, $R^5$ and U is as defined herein.

In other embodiments, provided herein is a compound having Formula (IV) or a stereoisomer, a geometric isomer, a tautomer, an N-oxide, a hydrate, a solvate, a metabolite, a pharmaceutically acceptable salt or a prodrug thereof,

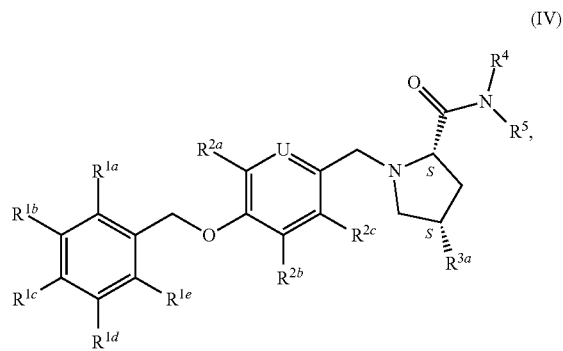

(IV)

wherein each $R^{1a}$, $R^{1b}$, $R^{1c}$, $R^{1d}$, $R^{1e}$, $R^{2a}$, $R^{2b}$, $R^{2c}$, $R^{3a}$, $R^4$, $R^5$ and U is as defined herein.

In still other embodiments, provided herein is a compound having Formula (V) or a stereoisomer, a geometric isomer, a tautomer, an N-oxide, a hydrate, a solvate, a metabolite, a pharmaceutically acceptable salt or a prodrug thereof,

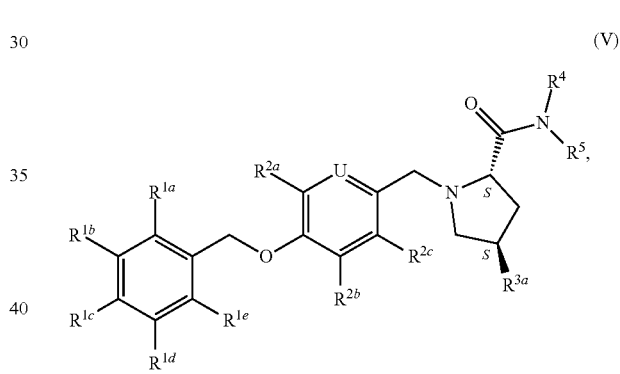

(V)

wherein each $R^{1a}$, $R^{1b}$, $R^{1c}$, $R^{1d}$, $R^{1e}$, $R^{2a}$, $R^{2b}$, $R^{2c}$, $R^{3a}$, $R^4$, $R^5$ and U is as defined herein.

In other aspect, provided herein is a pharmaceutical composition comprising the compound of Formula (I), (II), (III), (IV) or (V).

In some embodiments, the pharmaceutical composition disclosed herein optionally further comprises a pharmaceutically acceptable excipient, carrier, adjuvant or a combination thereof.

In other aspect, the present invention relates to use of the compound represented by formula (I), (II), (III), (IV) or (V) or the pharmaceutical composition in the manufacture of a medicament for preventing, treating or lessening a disease mediated by MAO-B in a subject.

In other aspect, the present invention relates to the compound represented by formula (I), (II), (III), (IV) or (V) or the pharmaceutical composition for use in preventing, treating or lessening a disease regulated by MAO-B in a subject.

In other aspect, the present invention relates to a method of preventing, treating or lessening a disease regulated by MAO-B comprising administering a therapeutically effective amount of the compound represented by formula (I), (II), (III), (IV) or (V) or the pharmaceutical composition to the subject.

In some embodiments, the disease regulated by MAO-B is a neurodegenerative disease, psychosis or cancer.

In some embodiments, the neurodegenerative disease is Parkinson's disease, cerebral ischemia, Alzheimer's disease, amyotrophic lateral sclerosis, bovine spongiform encephalopathy, Huntington's chorea, Creutzfeldt-Jakob disease, ataxia telangiectasia, cerebellar atrophy, spinal muscular atrophy, primary lateral sclerosis or multiple sclerosis.

In other aspect, provided herein is a method of preparing, separating or purifying the compound of Formula (I), (II), (III), (IV) or (V).

The biological test results show that the compound of the invention has good inhibitory effect on the activity of MAO-B and can be used as a good drug for treating Parkinson's disease.

Any embodiment disclosed herein can be combined with other embodiments as long as they are not contradictory to one another, even though the embodiments are described under different aspects of the invention. In addition, any technical feature in one embodiment can be applied to the corresponding technical feature in other embodiments as long as they are not contradictory to one another, even though the embodiments are described under different aspects of the invention.

The foregoing merely summarizes certain aspects disclosed herein and is not intended to be limiting in nature. These aspects and other aspects are described more fully below. All references of this specification are incorporated herein by reference in their entirety. In the event that one or more of the incorporated literature, patents, and similar materials differs from or contradicts this application, this application controls.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limiting to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994.

Additionally, general principles of organic chemistry are described in "Organic Chemistry", Thomas Sorrell, University Science Books, Sausalito: 1999, and Smith et al., "March's Advanced Organic Chemistry", John Wiley & Sons, New York: 2007, the entire contents of which are hereby incorporated by reference.

The grammatical articles "a", "an" and "the", as used herein, are intended to include "at least one" or "one or more" unless otherwise indicated herein or clearly contradicted by the context.

Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, "patient" refers to a human (including adults and children) or other animal. In one embodiment, "patient" refers to a human.

The term "comprise" is an open expression, it means comprising the contents disclosed herein, but doesn't exclude other contents.

The term "unsaturated" refers to a moiety having one or more units of unsaturation.

The term "stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

The term "chiral" refers to molecules which have the property of non-superimposability of the mirror image partner, while the term "achiral" refers to molecules which are superimposable on their mirror image partner.

The term "enantiomers" refers to two stereoisomers of a compound which are non-superimposable mirror images of one another.

The term "racemate" or "racemic mixture" refers to an equimolar mixture of two enantiomers lacking optical activity.

The term "diastereomer" refers to a stereoisomer with two or more centers of chirality and whose molecules are not mirror images of one another. Diastereomers have different physical properties, e.g. melting points, boiling points, spectral properties or biological activities. A mixture of diastereomers may be separated under high resolution analytical procedures such as electrophoresis and chromatography such as HPLC.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994, all of which are incorporated herein by reference. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compound(s) disclosed herein can be present in racemic or enantiomerically enriched, for example the (R)-, (S)- or (R,S)-configuration.

In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixture of stereoisomers can be separated on the basis of the physicochemical differences of the constituents, into the pure or substantially pure geometric isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., Enantiomers, Racemates and Resolutions (Wiley Interscience, New York, 1981); Principles of Asymmetric Synthesis ($2^{nd}$ Ed. Robert E. Gawley, Jeffrey Aubé, Elsevier, Oxford, U K, 2012); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, Ind. 1972); Chiral Separation Techniques: A Practical Approach (Subramanian, G. Ed., Wiley-VCH Verlag GmbH & Co. KGaA, Weinheim, Germany, 2007).

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. The specific example of phenol-keto tautomerisms is pyridin-4-ol and pyridin-4(1H)-one tautomerism. Unless otherwise stated, all tautomeric forms of the compounds disclosed herein are within the scope of the invention.

The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

The term "optional" or "optionally" refers to that a subsequently described event or circumstance may but need not occur, and that the description includes instances where the event or circumstance occurs and instances in which it does not. For example, "optional bond" means that the bond may or may not be present, and that the description includes single, double or triple bonds.

The terms "optionally substituted with . . . " and "unsubstituted or substituted with" can be used interchangeably, i.e. the structure is unsubstituted or substituted with one or more of the substituents described in the present invention, the substituents disclosed herein include, but are not limited to, D, F, Cl, Br, I, —OH, —$NH_2$, —$NO_2$, —CN, —SH, —COOH, —C(=O)$NH_2$, —C(=O)$NHCH_3$, —C(=O)N($CH_3$)$_2$, —C(=O)-alkyl, —C(=O)-alkoxy, alkyl, alkenyl, alkynyl, alkoxy, alkylthio, alkylamino, haloalkyl, haloalkoxy, hydroxy-substituted alkyl, -alkylene-cycloalkyl, -alkylene-heterocyclyl, -alkylene-aryl, -alkylene-heteroaryl, cycloalkyl, heterocyclyl, aryl, heteroaryl, and so on.

In general, the term "substituted" refers to the replacement of one or more hydrogen radicals in a given structure or radical with a specified substituent. Unless otherwise indicated, a substituent may substitute at any substitutable position of a radical. When more than one positions of a given structure can be substituted with one or more specified substituents, the substituents may be either the same or different at each position.

Furthermore, what need to be explained is that the phrase "each . . . is independently" and "each of . . . and . . . is independently", unless otherwise stated, should be broadly understood. The specific options expressed by the same symbol are independent of each other in different groups; or the specific options expressed by the same symbol are independent of each other in same groups.

At various places in the present specification, substituents of compounds disclosed herein are disclosed in groups or in ranges. It is specifically intended that the invention includes each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "D" or "$^2$H" refers to a single deuterium atom.

The terms "halogen" and "halo" can be used interchangeably, which refer to Fluoro (F), Chloro (Cl), Bromo (Br), or Iodo (I).

The term "heteroatom" refers to oxygen, sulfur, nitrogen, phosphorus and silicon, including any oxidized form of nitrogen, sulfur, or phosphorus; primary, secondary, tertiary amines and quaternary ammonium salts forms; or a substitutable nitrogen of a heterocyclic ring, for example, N (as in 3,4-dihydro-2H-pyrrolyl), NH (as in pyrrolidinyl) or NR (as in N-substituted pyrrolidinyl, wherein R is the substituent described herein).

The term "alkyl" or "alkyl group" refers to a saturated linear or branched-chain monovalent hydrocarbon group of 1-20 carbon atoms, wherein the alkyl group is optionally substituted with one or more substituents described herein. In one embodiment, the alkyl group contains 1-6 carbon atoms. In other embodiment, the alkyl group contains 1-4 carbon atoms. In still other embodiment, the alkyl group contains 1-3 carbon atoms. Examples of the alkyl group include, but are not limited to, methyl (Me, —$CH_3$), ethyl (Et, —$CH_2CH_3$), n-propyl (n-Pr, —$CH_2CH_2CH_3$), i-propyl (i-Pr, —$CH(CH_3)_2$), n-butyl (n-Bu, —$CH_2CH_2CH_2CH_3$), i-butyl (i-Bu, —$CH_2CH(CH_3)_2$), s-butyl (s-Bu, —$CH(CH_3)CH_2CH_3$), t-butyl (t-Bu, —$C(CH_3)_3$), and the like.

The term "alkylene" refers to a saturated divalent hydrocarbon group derived from a straight or branched chain saturated hydrocarbon by the removal of two hydrogen atoms. Unless otherwise specified, the alkylene group contains 1-12 carbon atoms. In some embodiments, the alkylene group contains 1-6 carbon atoms. In other embodiments, the alkylene group contains 1-4 carbon atoms. In still other embodiments, the alkylene group contains 1-3 carbon atoms. In yet other embodiments, the alkylene group contains 1-2 carbon atoms. And alkylene group is exemplified by methylene (—$CH_2$—), ethylene (—$CH_2CH_2$—), isopropylene (—$CH(CH_3)CH_2$—), and the like. Wherein the alkylene group is optionally substituted with one or more substitutents described herein.

The term "alkenyl" refers to linear or branched-chain monovalent hydrocarbon radical of 2 to 12 carbon atoms with at least one site of unsaturation, i.e., a carbon-carbon, $sp^2$ double bond, wherein the alkenyl radical may be optionally substituted with one or more substituents described herein, and includes radicals having "cis" and "trans" orientations, or alternatively, "E" and "Z" orientations. In some embodiments, the alkenyl contains 2 to 8 carbon atoms. In other embodiments, the alkenyl contains 2 to 6 carbon atoms. In still other embodiments, the alkenyl contains 2 to 4 carbon atoms. Some non-limiting examples of the alkenyl group include ethenyl or vinyl (—CH=$CH_2$), allyl (—$CH_2$CH=$CH_2$), 1-propenyl (propenyl, —CH=CH—$CH_3$), and the like.

The term "alkynyl" refers to a linear or branched-chain monovalent hydrocarbon radical of 2 to 12 carbon atoms with at least one site of unsaturation, i.e., a carbon-carbon, sp triple bond, wherein the alkynyl radical may be optionally substituted with one or more substituents described herein. In some embodiments, the alkynyl contains 2 to 8 carbon atoms. In other embodiments, the alkynyl contains 2 to 6 carbon atoms. In still other embodiments, the alkynyl contains 2 to 4 carbon atoms. Examples of such group include, but are not limited to, ethynyl (—C≡CH), propargyl (—$CH_2$C≡CH), 1-propynyl (propynyl, —C≡C—$CH_3$), and the like.

The term "alkoxy" refers to an alkyl group, as previously defined, attached to the parent molecular moiety via an oxygen atom. Unless otherwise specified, the alkoxy group contains 1-12 carbon atoms. In one embodiment, the alkoxy group contains 1-6 carbon atoms. In other embodiment, the alkoxy group contains 1-4 carbon atoms. In still other embodiment, the alkoxy group contains 1-3 carbon atoms. The alkoxy group may be optionally substituted with one or more substituents disclosed herein.

Examples of the alkoxy group include, but are not limited to, methoxy (MeO, —$OCH_3$), ethoxy (EtO, —$OCH_2CH_3$), 1-propoxy (n-PrO, n-propoxy, —$OCH_2CH_2CH_3$), 2-propoxy (i-PrO, isopropoxy, —$OCH(CH_3)_2$), 1-butoxy (n-BuO, n-butoxy, —$OCH_2CH_2CH_2CH_3$), 2-methyl-1-propoxy (i-BuO, i-butoxy, —$OCH_2CH(CH_3)_2$), 2-butoxy (s-BuO, s-butoxy, —$OCH(CH_3)CH_2CH_3$), 2-methyl-2-propoxy (t-BuO, t-butoxy, —$OC(CH_3)_3$), and the like.

The term "alkylthio" refers to an alkyl group, as previously defined, attached to the parent molecular moiety via a sulfur atom. Unless otherwise specified, the alkylthio group contains 1-12 carbon atoms. In one embodiment, the alkylthio group contains 1-6 carbon atoms. In other embodiment, the alkylthio group contains 1-4 carbon atoms. In still other embodiment, the alkylthio group contains 1-3 carbon atoms. The alkylthio group may be optionally substituted with one or more substituents disclosed herein.

Examples of the alkylthio group include, but are not limited to, methylthio (MeS, —$SCH_3$), ethylthio (EtS, —$SCH_2CH_3$), 1-propylthio (n-PrS, n-propylthio, —$SCH_2CH_2CH_3$), 2-propylthio (i-PrS, i-propylthio, —$SCH(CH_3)_2$), 1-butylthio (n-BuS, n-butylthio, —$SCH_2CH_2CH_2CH_3$), 2-methyl-1-propylthio (i-BuS, i-butylthio, —$SCH_2CH(CH_3)_2$), 2-butylthio (s-BuS, s-butylthio, —$SCH(CH_3)CH_2CH_3$), 2-methyl-2-propylthio (t-BuS, t-butylthio, —$SC(CH_3)_3$), and the like.

The term "alkylamino" comprises "N-alkylamino" and "N,N-dialkylamino", that is an amino group is independently substituted with one or two alkyl radicals and wherein the alkyl group is as defined herein. Suitable alkylamino radical may be monoalkylamino or dialkylamino. Examples of the alkylamino radical include, but are not limited to, N-methylamino (methylamino), N-ethylamino (ethylamino), N,N-dimethylamino (dimethylamino), N,N-diethylamino (diethylamino), and the like. And wherein the alkylamino radical is optionally substituted with one or more substituents described herein.

The term "hydroxy-substituted alkyl" refers to an alkyl group substituted with one or more hydroxy groups, wherein the alkyl is as defined herein. Examples of such group include, but are not limited to, hydroxymethyl, 2-hydroxyethyl, 2-hydroxy-1-propyl, 3-hydroxy-1-propyl, 2,3-dihydroxypropyl, and the like.

The term "haloalkyl" refers to an alkyl group substituted with one or more halo groups, wherein the alkyl is as defined herein. Examples of such group include, but are not limited to, —$CHF_2$, —$CF_3$, —$CHFCH_2F$, —$CF_2CHF_2$, —$CH_2CF_3$, —$CHFCH_3$, —$CH_2CH_2F$, —$CF_2CH_3$, —$CH_2CF_2CHF_2$ and the like.

In some embodiments, $C_1$-$C_6$ haloalkyl include fluoro substituted $C_1$-$C_6$ alkyl; In other embodiments, $C_1$-$C_4$ haloalkyl include fluoro substituted $C_1$-$C_4$ alkyl; In still other embodiments, $C_1$-$C_2$ haloalkyl include fluoro substituted $C_1$-$C_2$ alkyl.

The term "haloalkoxy" refers to an alkoxy group substituted with one or more halo groups, wherein the alkyl is as defined herein. Examples of such group include, but are not limited to, —$OCHF_2$, —$OCF_3$, —$OCHFCH_2F$, —$OCF_2CHF_2$, —$OCH_2CF_3$, —$OCHFCH_3$, —$OCH_2CH_2F$, —$OCF_2CH_3$, —$OCH_2CF_2CHF_2$, and the like. In some embodiments, $C_1$-$C_6$ haloalkoxy include fluoro substituted $C_1$-$C_6$ alkoxy; In the other embodiments, $C_1$-$C_4$ haloalkoxy include fluoro substituted $C_1$-$C_4$ alkoxy; In the still other embodiments, $C_1$-$C_2$ haloalkoxy include fluoro substituted $C_1$-$C_2$ alkoxy.

The term "consisting of n ring atoms" or "n-membered" as used interchangeably herein, wherein n is an integer, typically describes the number of ring-forming atoms in a moiety where the number of ring-forming atoms is n. For example, 5-10 membered heteroaryl refers to heteroaryl consisting of 5, 6, 7, 8, 9 or 10 ring atoms. Also, piperidinyl is a heterocyclyl consisting of 6 ring atoms or 6 membered heterocyclyl, and pyridyl is a heteroaryl consisting of 6 ring atoms or 6 membered heteroaryl.

The term "carbocyclyl", "carbocycle" or "carbocyclic ring" refers to a monovalent or multivalent, nonaromatic, saturated or partially unsaturated ring having 3 to 12 carbon atoms as a monocyclic, bicyclic or tricyclic ring system. A carbobicyclyl group includes a spiro carbobicyclyl group or a fused carbobicyclyl group. Suitable carbocyclyl groups include, but are not limited to, cycloalkyl, cycloalkenyl and cycloalkynyl. Further examples of carbocyclyl groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. And wherein the carbocyclyl group is optionally substituted with one or more substituents described herein.

The term "cycloalkyl" refers to a monovalent or multivalent saturated ring having 3 to 12 carbon atoms as a monocyclic, bicyclic, or tricyclic ring system. And wherein the bicyclic or tricyclic ring system may include fused ring, bridged ring and spiro ring. In some embodiments, the cycloalkyl group contains 3 to 10 carbon atoms. In other embodiments, the cycloalkyl group contains 3 to 8 carbon atoms. In still other embodiments, the cycloalkyl group contains 3 to 6 carbon atoms. Some non-limiting examples of the cycloalkyl group include cyclopropyl, cyclobutyl, cyclopentyl, cyclohexyl, and the like. The cycloalkyl radical is optionally substituted with one or more substituents described herein.

The term "heterocycle", "heterocyclyl", or "heterocyclic ring" as used interchangeably herein refers to a nonaromatic, saturated or partially unsaturated monocyclic, bicyclic or tricyclic ring system containing 3-12 ring atoms, wherein the bicyclic or tricyclic ring system may include fuse ring, bridged ring and spiro ring. Wherein one or more atoms on the ring each are independently replaced by heteroatom, the heteroatom is as defined herein. In some embodiments, the heterocyclyl group is a monocyclic heterocyclyl having 3-8 ring members (e.g., 2 to 6 carbon atoms and 1 to 3 heteroatoms selected from N, O, P and S, wherein the S or P is optionally substituted with one or more oxygen atoms to provide the group SO or $SO_2$, PO or $PO_2$); in other embodiments, the heterocyclyl group is a monocyclic heterocyclyl having 3-6 ring members (e.g., 2 to 5 carbon atoms and 1 to 3 heteroatoms selected from N, O, P and S, wherein the S or P is optionally substituted with one or more oxygen atoms to provide the group SO or $SO_2$, PO or $PO_2$); in still other embodiments, the heterocyclyl group is a bicyclic heterocyclyl having 7-12 ring members (e.g., 4 to 9 carbon atoms and 1 to 3 heteroatoms selected from N, O, P and S, wherein the S or P is optionally substituted with one or more oxygen atoms to provide the group SO or $SO_2$, PO or $PO_2$); and wherein the heterocyclyl group is optionally substituted with one or more substituents described herein.

The ring atom of the heterocyclyl may be a carbon radical or heteroatom radical. A —$CH_2$— group of the ring can optionally be replaced by a —C(=O)— group. Ring sulfur atoms may be optionally oxidized to form S-oxides, and ring nitrogen atoms may be optionally oxidized to form N-oxides. Some non-limiting examples of the heterocyclyl group include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, 2-oxa-5-azabicyclo[2.2.1]hept-5-yl, and the like. Some non-limiting examples of heterocyclyl wherein —$CH_2$— group is replaced by —C(=O)— moiety include 2-oxopyrrolidinyl, oxo-1,3-thiazolidinyl, 2-piperidinonyl, 3,5-dioxopiperidinyl, pyrimidinedione-yl, and the like. Some non-limiting examples of the heterocyclyl group of which the ring sulfur atom is oxidized include sulfolanyl, 1,1-dioxo-thiomorpholinyl, and the like. The heterocyclyl group is optionally substituted with one or more substituents described herein.

The term "aryl" refers to monocyclic, bicyclic and tricyclic carbocyclic ring systems having a total of six to fourteen ring members, or six to twelve ring members, or six to ten ring members, wherein at least one ring in the system is aromatic, wherein each ring in the system contains 3 to 7 ring members. The aryl group is generally, but not necessarily bonded to the parent molecule through an aromatic ring of the aryl group. The term "aryl" and "aromatic ring" can be used interchangeably herein. Examples of aryl ring may include phenyl, naphthyl, indenyl and anthryl. The aryl radical is optionally substituted with one or more substituents described herein.

The term "heteroaryl" refers to monocyclic, bicyclic and tricyclic ring systems having a total of five to twelve ring members, or five to ten ring members, or five to six ring members, wherein at least one ring in the system is aromatic, and in which at least one ring member is selected from heteroatom, and wherein each ring in the system contains 5 to 7 ring members. The heteroaryl group is generally, but not necessarily bonded to the parent molecule through an aromatic ring of the heteroaryl group. The term "heteroaryl" may be used interchangeably with the term "heteroaryl ring", "aromatic heterocyclic" or the term "heteroaromatic compound". The heteroaryl group is optionally substituted with one or more substituents disclosed herein. In one embodiment, a 5-10 membered heteroaryl comprises 1, 2, 3 or 4 heteroatoms independently selected from O, S and N.

Some non-limiting examples of the heteroaryl ring include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles, but not limited to: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl, or [1,2,4]triazolo[1,5-a]pyridyl, and the like.

The term "prodrug" refers to a compound that is transformed in vivo into a compound of Formula (I), (II), (III), (IV) or (V). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_{1-24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound.

A "metabolite" is a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

A "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in J. Pharmaceutical Sciences, 1977, 66: 1-19, which is incorporated herein by reference. Some non-limiting examples of pharmaceutically acceptable and nontoxic salts include salts formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other salts derived from pharmaceutically acceptable and nontoxic acids include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate, and the like. Pharmaceutically acceptable salts derived from appropriate bases include alkali metal salt, alkaline earth metal salt, ammonium and $N^+(C_{1-4}$ alkyl$)_4$ salts. Representative alkali metal salts or alkaline earth metal salts include sodium, lithium, potassium, calcium, magnesium, and the like. This invention also envisions the quaternization of any basic nitrogen-containing groups of the compounds disclosed herein. Water or oil soluble or dispersable products may be obtained by such quaternization. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid, ethanolamine or a combination thereof. The term "hydrate" refers to the complex where the solvent molecule is water.

The term "hydrate" can be used when said solvent is water. In one embodiment, one solvent molecule is associated with one molecule of the compounds disclosed herein, such as a hydrate. In another embodiment, more than one solvent molecule may be associated with one molecule of the compounds disclosed herein, such as a dihydrate. In still another embodiment, less than one solvent molecule may be associated with one molecule of the compounds disclosed herein, such as a hemihydrate. Furthermore, all the solvates of the invention retain the biological effectiveness of the non-hydrate form of the compounds disclosed herein.

"A compound of the invention", "the compound described in the invention", "the compound of the invention" or other similar descriptions, all represent the compound of any formula of the invention, i.e. the compound of formula (I), (II), (III), (IV) or (V) of the invention.

The term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

The term "preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

Pyrrolidineamide derivatives, pharmaceutically acceptable salts thereof, formulations and compositions thereof of the invention can inhibit the activity of MAO-B, and they have potential uses for treating neurodegenerative diseases, especially Parkinson's disease.

Unless otherwise stated, all stereoisomers, geometric isomers, tautomers, N-oxides, hydrates, solvates, metabolites, pharmaceutically acceptable salts and their prodrugs of the compounds disclosed herein are within the scope of the invention.

All stereoisomers of the structure disclosed herein are considered within the scope of the invention whether the stereochemistry of the structure is indicated or not, and which are interpreted as disclosed compounds of the invention and included in the invention. When the stereochemistry of a structure is indicated by solid wedge or dash line, the stereoisomer of the structure is definite.

N-oxides of the compound disclosed herein are also included in the invention. N-oxides of the compound of the invention can be prepared by oxidizing corresponding nitrogen-containing alkaline substances with common oxidants (hydrogen peroxide) under a rising temperature in the presence of an acid, such as acetic acid, or by reacting with peracid in a suitable solvent, e.g. in dichloromethane, ethyl acetate or methyl acetate react with peracetic acid, by reacting with 3-chloroperoxybenzoic acid in chloroform or dichloromethane.

The compound of Formula (I), (II), (III), (IV) or (V) can exist in salt forms. In one embodiment, the salt is a pharmaceutically acceptable salt thereof. The phrase "pharmaceutically acceptable" refers to that the substance or composition must be chemically and/or toxicologically compatible with the other ingredients comprising a formulation, and/or the mammal being treated therewith. In other embodiment, the salt is not necessarily a pharmaceutically acceptable salt and can be an intermediate for the preparation and/or purification of the compound of the Formula (I), (II), (III), (IV) or (V), and/or for the separation of the enantiomers of the Formula (I), (II), (III), (IV) or (V).

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent isotopically unenriched forms as well as isotopically enriched forms of the compounds. Compounds in isotopically enriched forms have a structure represented by the formula provided herein, excepting that one or more atoms are replaced by atoms with selected atomic mass or mass numbers. Examples of isotopes that can be incorporated into compounds of the invention include isotopes of hydrogen, carbon, nitrogen, oxygen, phosphorous, fluorine, and chlorine, such as $^2$H (deuterium, D), $^3$H, $^{11}$C, $^{13}$C, $^{14}$C, $^{15}$N, $^{17}$O, $^{18}$O, $^{18}$F, $^{31}$P, $^{32}$P, $^{35}$S, $^{36}$Cl, $^{125}$I, respectively.

In other aspect, provided herein is a preparation of intermediate of the compound of Formula (I), (II), (III), (IV) or (V).

In other aspect, provided herein is a pharmaceutical composition comprising the compound disclosed herein. In some embodiments, the pharmaceutical composition disclosed herein further comprises at least one of pharmaceutically acceptable carrier, excipient, adjuvant, solvent or a combination thereof. In other embodiment, the pharmaceutical composition can be liquid, solid, semi-solid, gel or spray.

DESCRIPTION OF COMPOUNDS OF THE INVENTION

The pyrrolidineamide derivatives, pharmaceutically acceptable salts thereof, formulations and compositions thereof of the invention have inhibition on the activity of MAO-A and MAO-B, especially have selective inhibition on the activity of MAO-B, so they have potential use for the treatment of neurodegenerative diseases, especially Parkinson's disease. The present invention further describes the synthetic method of the compound. The compounds of the invention show good bioactivity.

In one aspect, provided herein is a compound having Formula (I) or a stereoisomer, a geometric isomer, a tautomer, an N-oxide, a hydrate, a solvate, a metabolite, a pharmaceutically acceptable salt or a prodrug thereof,

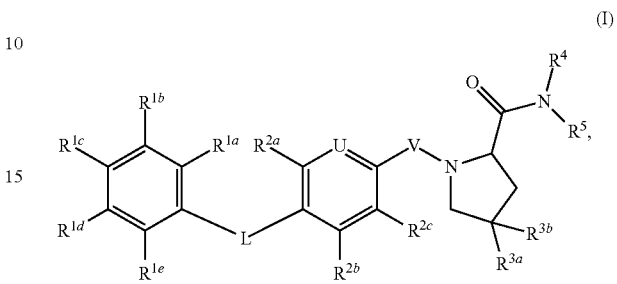

(I)

wherein each $R^{1a}$, $R^{1b}$, $R^{1c}$, $R^{1d}$, $R^{1e}$, $R^{2a}$, $R^{2b}$, $R^{2c}$, $R^{3a}$, $R^{3b}$, $R^4$, $R^5$, L, U and V is as defined herein.

In some embodiments, L is —CH$_2$O— or —OCH$_2$—.

In some embodiments, U is CR$^u$ or N.

In some embodiments, V is —CH$_2$—, —CH$_2$CH$_2$— or a single bond.

In some embodiments, each $R^{1a}$, $R^{1b}$, $R^{1c}$, $R^{1d}$ and $R^{1e}$ is independently H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—(C$_1$-C$_6$ alkyl), —C(=O)—(C$_1$-C$_6$ alkoxy), C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ haloalkoxy, C$_1$-C$_6$ alkylthio, C$_1$-C$_6$ alkylamino, hydroxy-substituted C$_1$-C$_6$ alkyl, C$_3$-C$_8$ cycloalkyl, 3-8 membered heterocyclyl, C$_6$-C$_{10}$ aryl or 5-10 membered heteroaryl.

In some embodiments, R is H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—(C$_1$-C$_6$ alkyl), —C(=O)—(C$_1$-C$_6$ alkoxy), C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ haloalkoxy, C$_1$-C$_6$ alkylthio, C$_1$-C$_6$ alkylamino, hydroxy-substituted C$_1$-C$_6$ alkyl, C$_3$-C$_5$ cycloalkyl, 3-8 membered heterocyclyl, C$_6$-C$_{10}$ aryl or 5-10 membered heteroaryl.

In some embodiments, each $R^{2a}$, $R^{2b}$ and $R^{2c}$ is independently H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—(C$_1$-C$_6$ alkyl), —C(=O)—(C$_1$-C$_6$ alkoxy), C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ haloalkoxy, C$_1$-C$_6$ alkylthio, C$_1$-C$_6$ alkylamino, hydroxy-substituted C$_1$-C$_6$ alkyl, C$_3$-C$_8$ cycloalkyl, 3-8 membered heterocyclyl, C$_6$-C$_{10}$ aryl or 5-10 membered heteroaryl.

In some embodiments, $R^{3a}$ is D, F, Cl, Br, I, C$_1$-C$_6$ alkyl, C$_1$-C$_6$ haloalkyl, C$_2$-C$_6$ alkoxy, C$_1$-C$_6$ haloalkoxy or hydroxy-substituted C$_1$-C$_6$ alkyl.

In some embodiments, $R^{3b}$ is H, D, F, Cl, Br, I, C$_1$-C$_6$ alkyl, C$_1$-C$_6$ haloalkyl, C$_1$-C$_6$ alkoxy, C$_1$-C$_6$ haloalkoxy or hydroxy-substituted C$_1$-C$_6$ alkyl.

In some embodiments, each $R^4$ and $R^5$ is independently H, D, C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ haloalkoxy, C$_1$-C$_6$ alkylthio, C$_1$-C$_6$ alkylamino, hydroxy-substituted C$_1$-C$_6$ alkyl, C$_3$-C$_8$ cycloalkyl, 3-8 membered heterocyclyl, C$_6$-C$_{10}$ aryl or 5-10 membered heteroaryl, wherein each of the C$_1$-C$_6$ alkyl, C$_2$-C$_6$ alkenyl, C$_2$-C$_6$ alkynyl, C$_1$-C$_6$ haloalkyl, C$_1$-C$_6$ alkoxy, C$_1$-C$_6$ haloalkoxy, C$_1$-C$_6$ alkylthio, C$_1$-C$_6$ alkylamino, hydroxy-substituted C$_1$-C$_6$ alkyl, C$_3$-C$_8$ cycloalkyl, 3-8 membered heterocyclyl, $C_6$-$C_{10}$ aryl and 5-10 membered heteroaryl is independently and optionally substituted with 1, 2, 3, 4 or 5 substituents selected from D, F, Cl, Br, I, —OH, —NH$_2$, —NO$_2$, —CN, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl or $C_6$-$C_{10}$ aryl.

In some embodiments, each $R^{1a}$, $R^{1b}$, $R^{1c}$, $R^{1d}$ and $R^{1e}$ is independently H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—($C_1$-$C_4$ alkyl), —C(=O)—($C_1$-$C_4$ alkoxy), $C_1$-$C_4$ alkyl, $C_2$-$C_4$ alkenyl, $C_2$-$C_4$ alkynyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ alkylamino, hydroxy-substituted $C_1$-$C_4$ alkyl, $C_3$-$C_6$ cycloalkyl, 3-6 membered heterocyclyl, $C_6$-$C_{10}$ aryl or 5-10 membered heteroaryl.

In other embodiments, each $R^{1a}$, $R^{1b}$, $R^{1c}$, $R^{1d}$ and $R^{1e}$ is independently H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—CH$_3$, —C(=O)—OCH$_3$, methyl, ethyl, n-propyl, i-propyl, allyl, propenyl, propargyl, propinyl, —CHF$_2$, —CF$_3$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofiranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl or quinolyl.

In some embodiments, R is H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—($C_1$-$C_4$ alkyl), —C(=O)—($C_1$-$C_4$ alkoxy), $C_1$-$C_4$ alkyl, $C_2$-$C_4$ alkenyl, $C_2$-$C_4$ alkynyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ alkylamino, hydroxy-substituted $C_1$-$C_4$ alkyl, $C_3$-$C_6$ cycloalkyl, 3-6 membered heterocyclyl, $C_6$-$C_{10}$ aryl or 5-10 membered heteroaryl.

In other embodiments, $R^u$ is H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—CH$_3$, —C(=O)—OCH$_3$, methyl, ethyl, n-propyl, i-propyl, allyl, propenyl, propargyl, propinyl, —CHF$_2$, —CF$_3$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofuranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl or quinolyl.

In some embodiments, each $R^{2a}$, $R^{2b}$ and $R^{2c}$ is independently H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—($C_1$-$C_4$ alkyl), —C(=O)—($C_1$-$C_4$ alkoxy), $C_1$-$C_4$ alkyl, $C_2$-$C_4$ alkenyl, $C_2$-$C_4$ alkynyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ alkylamino, hydroxy-substituted $C_1$-$C_4$ alkyl, $C_3$-$C_6$ cycloalkyl, 3-6 membered heterocyclyl, $C_6$-$C_{10}$ aryl or 5-10 membered heteroaryl.

In other embodiments, each $R^{2a}$, $R^{2b}$ and $R^{2c}$ is independently H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—CH$_3$, —C(=O)—OCH$_3$, methyl, ethyl, n-propyl, i-propyl, allyl, propenyl, propargyl, propinyl, —CHF$_2$, —CF$_3$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofiranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl or quinolyl.

In some embodiments, $R^{3a}$ is D, F, Cl, Br, I, $C_1$-$C_4$ alkyl, $C_1$-$C_4$ haloalkyl, $C_2$-$C_4$ alkoxy, $C_1$-$C_4$ haloalkoxy or hydroxy-substituted $C_1$-$C_4$ alkyl.

In other embodiments, $R^{3a}$ is D, F, Cl, Br, I, methyl, ethyl, n-propyl, i-propyl, —CHF$_2$, —CF$_3$, —CHFCH$_2$F, —CF$_2$CHF$_2$, —CH$_2$CF$_3$, —CH$_2$CF$_2$CHF$_2$, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, hydroxymethyl or 2-hydroxyethyl.

In some embodiments, $R^{3b}$ is H, D, F, Cl, Br, I, $C_1$-$C_4$ alkyl, $C_1$-$C_4$ haloalkyl, $C_1$-$C_4$ alkoxy, $C_1$-$C_4$ haloalkoxy or hydroxy-substituted $C_1$-$C_4$ alkyl.

In other embodiments, $R^{3b}$ is H, D, F, Cl, Br, I, methyl, ethyl, n-propyl, i-propyl, —CHF$_2$, —CF$_3$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, hydroxymethyl or 2-hydroxyethyl.

In some embodiments, each $R^4$ and $R^5$ is independently H, D, $C_1$-$C_4$ alkyl, $C_2$-$C_4$ alkenyl, $C_2$-$C_4$ alkynyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ alkylamino, hydroxy-substituted $C_1$-$C_4$ alkyl, $C_3$-$C_6$ cycloalkyl, 3-6 membered heterocyclyl, $C_6$-$C_{10}$ aryl or 5-10 membered heteroaryl, wherein each of the $C_1$-$C_4$ alkyl, $C_2$-$C_4$ alkenyl, $C_2$-$C_4$ alkynyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ alkylamino, hydroxy-substituted $C_1$-$C_4$ alkyl, $C_3$-$C_6$ cycloalkyl, 3-6 membered heterocyclyl, $C_6$-$C_{10}$ aryl and 5-10 membered heteroaryl is independently and optionally substituted with 1, 2, 3, 4 or 5 substituents selected from D, F, Cl, Br, I, —OH, —NH$_2$, —NO$_2$, —CN, $C_1$-$C_4$ alkyl, $C_1$-$C_4$ haloalkyl, $C_1$-$C_4$ alkoxy, $C_1$-$C_4$ haloalkoxy, $C_3$-$C_6$ cycloalkyl or $C_6$-$C_{10}$ aryl.

In other embodiments, each $R^4$ and $R^5$ is independently H, D, methyl, ethyl, n-propyl, i-propyl, allyl, propenyl, propargyl, propinyl, —CHF$_2$, —CF$_3$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofuranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl or quinolyl, wherein each of the methyl, ethyl, n-propyl, i-propyl, allyl, propenyl, propargyl, propinyl, —CHF$_2$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCHFCH$_2$F, —OCF$_2$CHF$_2$, —OCH$_2$CF$_3$, —OCH$_2$CF$_2$CHF$_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofuranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl and quinolyl is independently and optionally substituted with 1, 2, 3, 4 or 5 substituents selected from D, F, Cl, Br, I, —OH, —NH$_2$, —NO$_2$, —CN, methyl, ethyl, n-propyl, i-propyl, —CHF$_2$, —CF$_3$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, cyclopropyl, cyclobutyl, cyclopentyl, cyclohexyl, phenyl, indenyl or naphthyl.

In some embodiments, provided herein is a compound having Formula (II) or a stereoisomer, a geometric isomer, a tautomer, an N-oxide, a hydrate, a solvate, a metabolite, a pharmaceutically acceptable salt or a prodrug thereof,

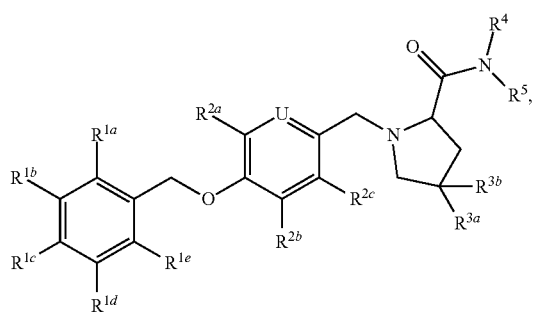

(II)

wherein each $R^{1a}$, $R^{1b}$, $R^{1c}$, $R^{1d}$, $R^{1e}$, $R^{2a}$, $R^{2b}$, $R^{2c}$, $R^{3a}$, $R^{3b}$, $R^4$, $R^5$ and U is as defined herein.

In other embodiments, provided herein is a compound having Formula (III) or a stereoisomer, a geometric isomer, a tautomer, an N-oxide, a hydrate, a solvate, a metabolite, a pharmaceutically acceptable salt or a prodrug thereof,

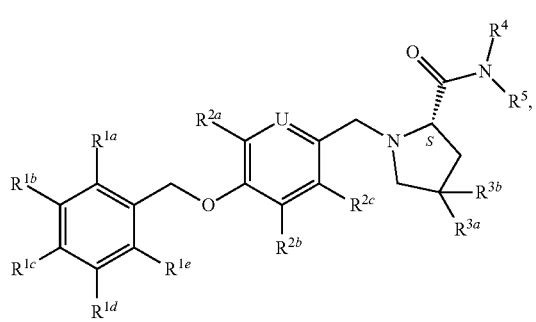

(III)

wherein each $R^{1a}$, $R^{1b}$, $R^{1c}$, $R^{1d}$, $R^{1e}$, $R^{2a}$, $R^{2b}$, $R^{2c}$, $R^{3a}$, $R^{3b}$, $R^4$, $R^5$ and U is as defined herein.

In other embodiments, provided herein is a compound having Formula (IV) or a stereoisomer, a geometric isomer, a tautomer, an N-oxide, a hydrate, a solvate, a metabolite, a pharmaceutically acceptable salt or a prodrug thereof,

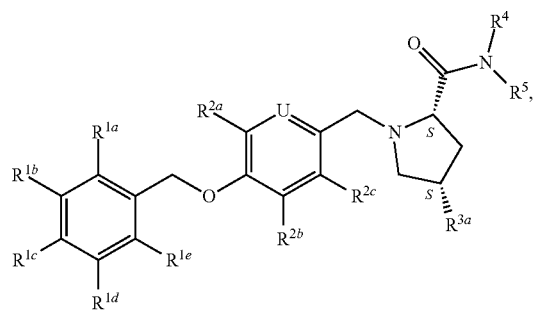

(IV)

wherein each $R^{1a}$, $R^{1b}$, $R^{1c}$, $R^{1d}$, $R^{1e}$, $R^{2a}$, $R^{2b}$, $R^{2c}$, $R^{3a}$, $R^4$, $R^5$ and U is as defined herein.

In still other embodiments, provided herein is a compound having Formula (V) or a stereoisomer, a geometric isomer, a tautomer, an N-oxide, a hydrate, a solvate, a metabolite, a pharmaceutically acceptable salt or a prodrug thereof,

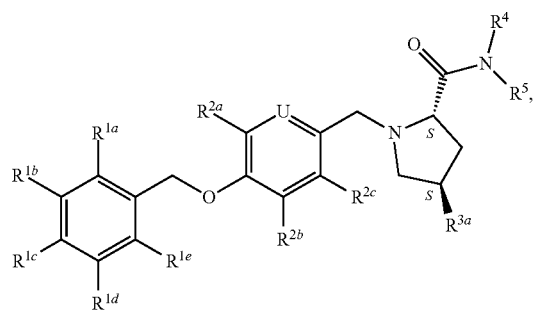

(V)

wherein each $R^{1a}$, $R^{1b}$, $R^{1c}$, $R^{1d}$, $R^{1e}$, $R^{2a}$, $R^{2b}$, $R^{2c}$, $R^{3a}$, $R^4$, $R^5$ and U is as defined herein.

In some embodiments, the compound disclosed herein has one of the following structures or a stereoisomer, a geometric isomer, a tautomer, an N-oxide, a hydrate, a solvate, a metabolite, a pharmaceutically acceptable salt or a prodrug thereof:

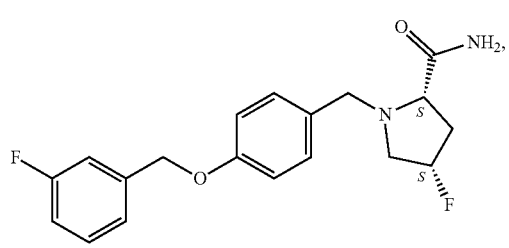

(1)

-continued
(2)
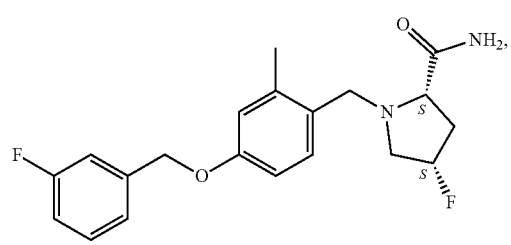
(3)
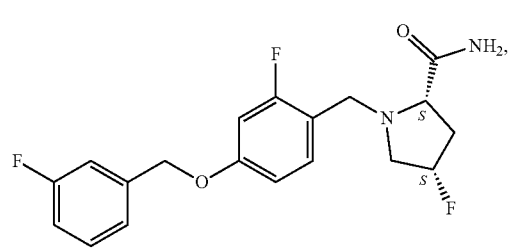
(4)
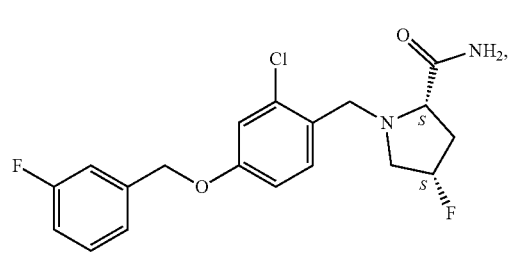
(5)
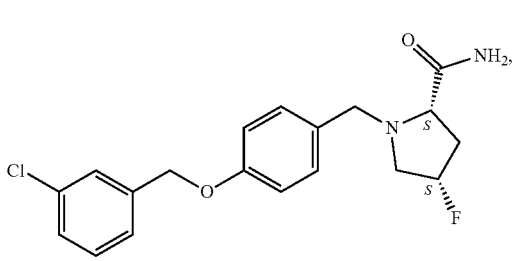
(6)
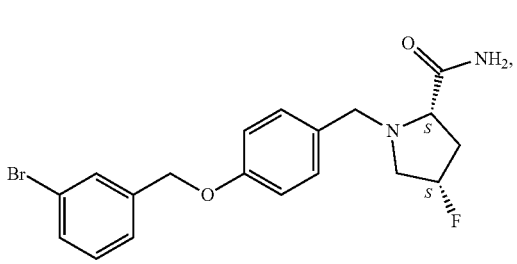
(7)
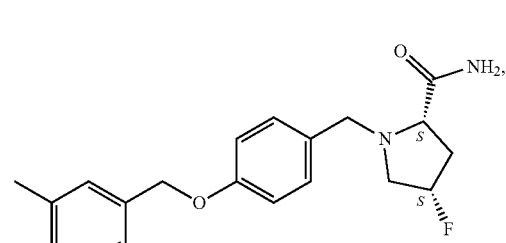
-continued
(8)
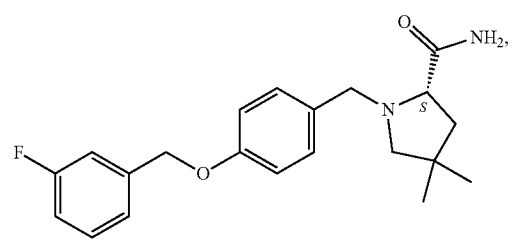
(9)
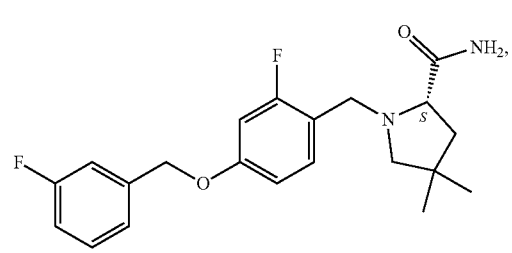
(10)
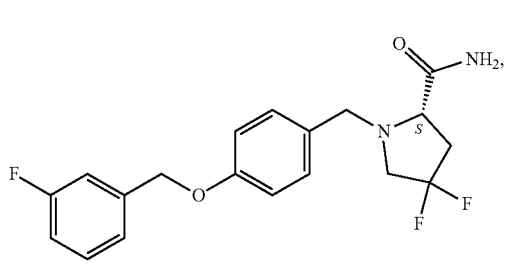
(11)
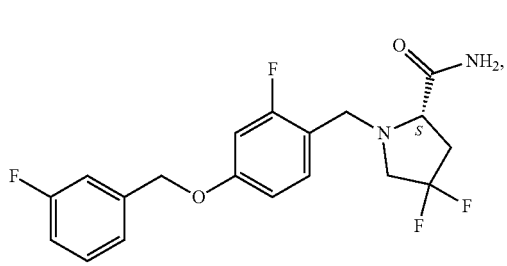
(12)
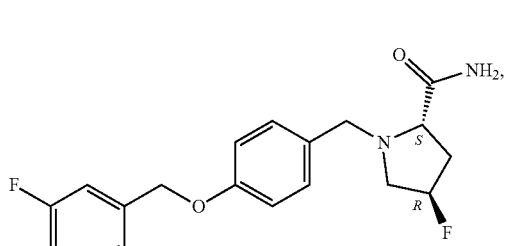
(13)
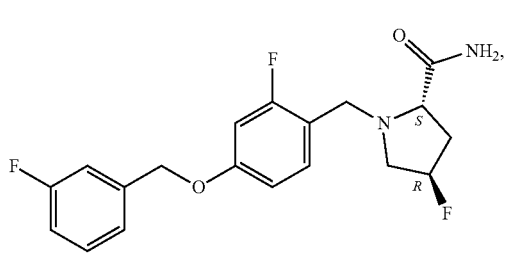

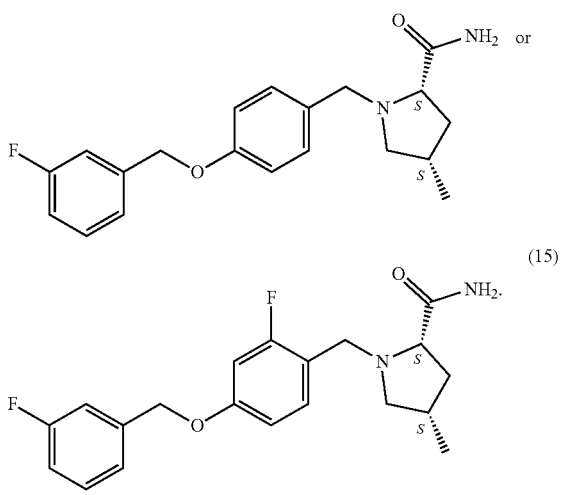

In other aspect, provided herein is a pharmaceutical composition comprising the compound of Formula (I), (II), (III), (IV) or (V).

In some embodiments, the pharmaceutical composition disclosed herein optionally further comprises a pharmaceutically acceptable excipient, carrier, adjuvant or a combination thereof.

In other aspect, the present invention relates to use of the compound represented by formula (I), (II), (III), (IV) or (V) or a composition thereof or a pharmaceutical composition in the manufacture of a medicament for preventing, treating or lessening a disease mediated by MAO-B in a patient.

In some embodiments, the disease regulated by MAO-B is a neurodegenerative disease, psychosis or cancer.

In some embodiments, the neurodegenerative disease is Parkinson's disease, cerebral ischemia, Alzheimer's disease, amyotrophic lateral sclerosis, bovine spongiform encephalopathy, Huntington's chorea, Creutzfeldt-Jakob disease, ataxia telangiectasia, cerebellar atrophy, spinal muscular atrophy, primary lateral sclerosis or multiple sclerosis.

In other aspect, provided herein is a method of preparing, separating or purifying the compound of Formula (I), (II), (III), (IV) or (V).

PHARMACEUTICAL COMPOSITION OF THE COMPOUND OF THE INVENTION AND PREPARATIONS AND ADMINISTRATION

The invention provides a pharmaceutical composition containing a therapeutic effective amount of the compound of formula (I), (II), (III), (IV) or (V) or an independent stereoisomer thereof, a racemic mixture or non-racemic mixture of the stereoisomer thereof, or a pharmaceutically acceptable salt or solvate thereof. In one embodiment of the invention, the pharmaceutical composition further comprises at least one pharmaceutically acceptable carrier, adjuvant or excipient, and optionally other treating and/or preventing ingredients.

A suitable carrier, adjuvant or excipient is well known for the technical person in the field and was described in detail in Ansel H. C. et al., Ansel's Pharmaceutical Dosage Forms and Drug Delivery Systems (2004) Lippincott, Williams & Wilkins, Philadelphia; Gennaro A. R. et al., Remington: The Science and Practice of Pharmacy (2000) Lippincott, Williams & Wilkins, Philadelphia; and Rowe R. C., Handbook of Pharmaceutical Excipients (2005) Pharmaceutical Press, Chicago.

"Pharmaceutically acceptable excipient" as used herein means a pharmaceutically acceptable material, mixture or vehicle involved in consistency to giving form or the pharmaceutical composition. Each excipient must be compatible with the other ingredients of the pharmaceutical composition when commingled, such that interactions which would substantially reduce the efficacy of the compound of the invention when administered to a patient and would result in pharmaceutically unacceptable compositions are avoided. In addition, each excipient must of course be of sufficiently high purity to render it pharmaceutically acceptable.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound of the present invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, humectants, chelating agents, plasticizers, viscosity increasing agents, antioxidants, preservatives, stabilizers, surfactants, and buffering agents.

The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

The pharmaceutical compositions of the invention are prepared using techniques and methods known to those skilled in the art. Some of the methods commonly used in the art are described in Remington's Pharmaceutical Sciences (Mack Publishing Company).

Therefore, another aspect of the present invention is related to a method for preparing a pharmaceutical composition, the pharmaceutical composition contains the compound disclosed herein and pharmaceutically acceptable excipient, carrier, adjuvant, vehicle or a combination thereof, the method comprises mixing various ingredients. The pharmaceutical composition containing the compound disclosed herein can be prepared at for example environment temperature and under barometric pressure.

The compound of the invention will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need thereof is capable of providing, directly or indirectly, a compound as otherwise described herein, or a metabolite or residue thereof.

In one embodiment, the compounds disclosed herein can be prepared to oral administration. In the other embodiment, the compounds disclosed herein can be prepared to inhalation administration. In the still other embodiment, the compounds disclosed herein can be prepared to nasal administration. In the yet other embodiment, the compounds disclosed herein can be prepared to transdermal administration. In the still yet other embodiments, the compounds disclosed herein can be prepared to topical administration.

For example, in addition to the active ingredients, solid oral formulations can also include: diluents such as lactose, glucose, sucrose, corn starch or potato starch; lubricants such as silicon dioxide, talc powder, stearic acid, magnesium stearate or calcium stearate and/or polyethylene glycol; adhesives such as starch, Arabic gum, gelatin, methyl cellulose, carboxymethyl cellulose, polyvinylpyrrolidone; disintegrants such as starch, alginic acid, alginate or sodium hydroxyacetate starch; effervescent mixtures; dyes; sweeteners; wetting agents such as lecithin, polysorbitol esters, lauryl sulfates; and substances used in pharmaceutical preparations that are generally non-toxic and pharmaceutically inactive. The pharmaceutical formulations can be prepared by a well-known method, such as mixing, granulation, tableting, sugar coating or film coating processes.

Oral formulations include sustained-release preparations that can be prepared in conventional ways, such as by coating tablets and granules.

The liquid dispersions used for oral administration may be syrups, emulsions and suspensions.

The pharmaceutical compositions provided herein may be provided as compressed tablets, tablet triturates, chewable lozenges, rapidly dissolving tablets, multiple compressed tablets, enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach.

Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Emulsions and suspensions may include natural gum, agar, sodium alginate, pectin, methyl cellulose, carboxymethyl cellulose or polyvinyl alcohol as carriers. Suspensions or solutions for intramuscular injection may contain pharmaceutically acceptable carriers and active compounds, the pharmaceutically acceptable carrier is, for example, sterile water, olive oil, ethyl oleate, glycols such as propylene glycol. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxy groups, such as propylene glycol and ethanol. Solutions for intravenous injection or drip intravenous infusion may include carriers such as sterile water or preferably in the form of sterile, aqueous isotonic saline solution, etc. Elixirs are clear, sweetened, and hydroalcoholic solutions. Syrup agents may contain a carrier such as sucrose or sucrose mixed with glycerol and/or mannitol and/or sorbitol, for example, sucrose aqueous solution, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

The pharmaceutical composition provided in the invention is prepared to a dosage form adapted for administration to a patient by inhalation, for example as a dry powder, an aerosol, a suspension, or a solution composition. In one embodiment, the invention is directed to a dosage form adapted for administration to a patient by inhalation as a dry powder. In other embodiment, the invention is directed to a dosage form adapted for administration to a patient by inhalation through a spayer. Dry powder compositions for delivery to the lung by inhalation typically comprise a compound disclosed herein as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318(1986).

Pharmaceutical compositions adapted for topical administration may be formulated as ointments, creams, suspensions, lotions, powders, solutions, pastes, gels, sprays, aerosols or oils. Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as *arachis* oil or castor oil, or a solvent such as polyethylene glycol Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

The compounds disclosed herein can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, polyepsilon-caprolactone, polyhydroxybutyric acid, polyorthoesters, polyacetals, polydihydroxypyrans, polycyanoacrylates and crosslinked or amphipathic block copolymers of hydrogels.

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

The pharmaceutical composition provided herein can be administered by rectal in suppository form, the drug was mixed with suitable non-irritating excipients such as cocoa oil and glycerol ester synthesized by polyethylene glycol, the mixture was solid at room temperature and can be released when liquefied or dissolved in the rectal cavity. Because of individual differences, the severity of symptoms between individuals will have great difference, and every drug has its unique therapeutic properties. Therefore, the exact way of administration, dosage form and treatment plan for each individual should be determined by a practicing physician.

The pharmaceutical compositions provided herein may be formulated as immediate or modified release dosage forms, including delayed-, sustained, pulsed-, controlled, targeted-, and programmed-release forms.

The term "therapeutically effective amount" as used herein, refers to the total amount of each active component that is sufficient to show a useful treatment effect. For example, the drug amount of administration or balance in the body sufficient to treat, cure, or alleviate symptoms of a disease. The effective amount required for a special treatment depends on a variety of factors, including diseases, the severity of the disease, the activity of the used specific drug, the mode of administration, the clearance rate of the specific drug, the duration of therapy, the combination of drugs, age, weight, gender, diet and patient's health, and so on. The description of other factors that need to be considered for "therapeutically effective amount" in this field can be found in Gilman et al., eds., Goodman And Gilman's: The Pharmacological Bases of Therapeutics, 8th ed., Pergamon Press, 1990; Remington's Pharmaceutical Sciences, 17th ed., Mack Publishing Company, Easton, Pa., 1990. The compound is administered by oral, intraperitoneal or intravenous at a dose of the therapeutically effective amount, such as 0.1-200 mg/kg, having activity in vivo.

The given optimally therapeutically effective amount can be easily determined by those skilled in the field, and basically varies according to the formulation strength, the administration mode and the development of the disease or disorder. In addition, specific factors related to the subjects, including age, weight, diet and administration time, will lead to a need to adjust the dose to an appropriate level of therapeutic effectiveness.

The term "administration" refers to provision of a therapeutically effective amount of medicine to an individual by oral, sublingual, intravenous, subcutaneous, percutaneous, intramuscular, intradermal, intrathecal, epidural, intraocular, intracranial, inhalation, rectal, vagina, etc. The pharmaceutical dosage forms include plaster, lotion, tablet, capsule, pill, dispersible powder, granule, suppository, sublimed preparation, lozenge, injection, aseptic solution or non-aqueous solution, suspension, emulsion, paster, etc. An active component is complexed with a non-toxic pharmaceutically acceptable carrier (such as glucose, lactose, gum arabic, gelatin, mannitol, starch paste, magnesium trisilicate, talcum powder, corn starch, keratin, silica gel, potato starch, urea, dextran, etc.).

The preferred route of administration varies with clinical characteristics. Dose changes must depend on situation of patients receiving treatment. Doctors will determine the appropriate dose according to individual status of patients. The therapeutically effective amount per unit dose depends on body weight, physiological function and the selected vaccination program. An amount of compounds per unit dose refer to the weight of the compound per each administration, excluding weight of carriers (the drug formulation contains carriers). Pharmaceutical compositions containing pyrrolidineamide derivatives as defined in formula (I), (II), (III), (IV) or (V) contain one or more active ingredients of about 0.1 mg to about 500 mg per unit of measurement, such as capsule, tablet, powder injection, teaspoon capacity, suppository, and more preferably, 1-10 mg.

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

The pharmaceutical compositions provided herein may be co-formulated with other active ingredients which do not impair the desired therapeutic action, or with substances that supplement the desired action.

In one embodiment, the therapeutic methods disclosed herein comprise administrating to a patient in need of the treatment a safe and effective amount of the compound of the invention or the pharmaceutical composition containing the compound of the invention. Each example disclosed herein comprises the method of treating the diseases comprising administrating to a patient in need of the treatment a safe and effective amount of the compound of the invention or the pharmaceutical composition containing the compound of the invention.

In one embodiment, the compound of the invention or the pharmaceutical composition thereof may be administered by any suitable route of administration, including both systemic administration and topical administration. Systemic administration includes oral administration, parenteral administration, transdermal administration and rectal administration. Parenteral administration is typically by injection or infusion, includes intravenous, intramuscular, subcutaneous injection or infusion. Topical administration includes application to the skin as well as intraocular, otic, intravaginal, inhaled and intranasal administration. In one embodiment, the compound of the invention or the pharmaceutical composition thereof may be administered orally. In another embodiment, the compound of the invention or the pharmaceutical composition thereof may be administered by inhalation. In one embodiment, the compound of the invention or the pharmaceutical composition thereof may be administered intranasally.

In one embodiment, the compound of the invention or the pharmaceutical composition thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for the compound of the invention or the pharmaceutical composition thereof depend on the pharmacokinetic properties of that compound, such as absorption, distribution, and half-life, which can be determined by the skilled artisan. In addition, suitable dosing regimens, including the duration such regimens are administered, for the compound of the invention or the pharmaceutical composition thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

The compounds of the present invention may be administered either simultaneously with, or before or after, one or more other therapeutic agents. The compounds of the present invention may be administered separately, by the same or different route of administration, or together in the same pharmaceutical composition as the other agents.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

USE OF THE COMPOUNDS AND PHARMACEUTICAL COMPOSITIONS

The compounds and pharmaceutical compositions provided by the invention can be used to prepare a medicament for preventing, treating or an alleviating disease regulated by MAO-B for patients, and also to prepare a medicament for preventing, treating or alleviating a neurodegenerative disease, psychosis or a cancer.

Specifically, the compound having the amount as which in the pharmaceutical composition of the present invention can effectively and selectively inhibit the activity of MAO-B.

Compounds disclosed herein would be useful for, but not limiting to, the prevention or treatment or alleviation of neurodegenerative diseases in a patient by administering to the patient a compound or a composition disclosed herein in an effective amount. The neurodegenerative diseases include, but are not limited to, Parkinson's disease, cerebral ischemia, Alzheimer's disease, amyotrophic lateral sclerosis, hearing loss caused by aging, dementia, retinal degeneration, macular degeneration, glaucoma, bovine spongiform encephalopathy, Huntington's chorea, Creutzfeldt-Jakob disease, ataxia telangiectasia, cerebellar atrophy, spinal muscular atrophy, primary lateral sclerosis or multiple sclerosis.

Compounds disclosed herein would be useful for, but not limiting to, the prevention or treatment or alleviation of psychosis in a patient by administering to the patient a compound or a composition disclosed herein in an effective amount. The psychosis is schizophrenia and/or an anxiety disorder, wherein the schizophrenia further includes but is not limited to a short-term mental disorder, delusion, affective schizophrenia and schizophrenic-like mental disorders; and wherein the anxiety disorder further includes but is not limited to a panic disorder, obsessive-compulsive disorder, post-traumatic stress disorder, social phobia or social anxiety disorder, and special phobia and general anxiety disorder.

Compounds disclosed herein would be useful for, but not limiting to, the prevention or treatment or alleviation of a cancer in a patient by administering to the patient a compound or a composition disclosed herein in an effective amount. The cancer further includes, but is not limited to, prostate cancer, breast cancer, testicular cancer, colorectal cancer, lung cancer, brain cancer, kidney cancer or blood cancer.

Besides being useful for human treatment, these compounds are also useful for veterinary treatment of animals such as companion animals, exotic animals and farm animals. In other embodiments, the animals disclosed herein include horses, dogs, and cats. As used herein, the compounds disclosed herein include the pharmaceutically acceptable derivatives thereof.

GENERAL SYNTHETIC PROCEDURES OF THE COMPOUND

For the purpose of describing the invention, the following examples are listed. It should be understood that, the invention is not limited to these examples, and the present invention only provide the method to practice the invention.

Generally, the compounds disclosed herein may be prepared by methods described herein, wherein the substituents are as defined for Formula (I), (II), (III), (IV) or (V) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Tianjin Fuchen Chemical Reagent Factory, Wuhan XinHuaYuanm Technology Development Co. Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexane, DMAC and DMF were treated with anhydrous sodium sulfate prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory.

$^1$H NMR spectra were recorded by Bruker 400 MHz or 600 MHz NMR spectrometer. $^1$H NMR spectra were obtained by using $CDCl_3$, DMSO-$d_6$, $CD_3OD$ or acetone-$d_6$ solutions (in ppm), with TMS (0 ppm) or chloroform (7.26 ppm) as the reference standard. When peak multiplicities are reported, the following abbreviations are used: s (singlet), d (doublet), t (triplet), q (quartet), m (multiplet), br (broadened), brs (broadened singlet), dd (doublet of doublets), ddd (doublet of doublet of doublets), dt (doublet of triplets), td (triplet of doublets), tt (triplet of triplets). Coupling constants J, when given, were reported in Hertz (Hz).

Low resolution mass spectrum (MS) data measurement condition: Agilent 6120 Quadrupole HPLC-MS (column type: Zorbax SB-C18, 2.1×30 mm, 3.5 micron, 6 min, flow rate 0.6 mL/min. Mobile phase: in the proportion of 5%-95% ($CH_3CN$ containing 0.1% of formic acid) in ($H_2O$ containing 0.1% of formic acid), using electrospray ionization (ESI), UV detection, at 210 nm/254 nm.

Pure compound was detected by Agilent 1260 pre-HPLC or Calesep pump 250 pre-HPLC (NOVASEP 50/80 mm DAC) with UV detection at 210/254 nm.

The following abbreviations are used throughout the specification:

DCM, $CH_2Cl_2$ dichloromethane
$CDCl_3$ chloroform-d

DMSO dimethylsulfoxide
DMSO-$d_6$ deuterated dimethyl sulfoxide
EtOAc, EA ethyl acetate
$CH_3OH$, MeOH methanol
Acetone acetone
$H_2O$ water
$Et_3N$ triethylamine
$NaBH_4$ Sodium borohydride
$PBr_3$ phosphorus tribromide
mmol, mM millimole
ng nanogram
μg microgram
g gram
s second(s)
min minute(s)
h hour(s)
$K_2CO_3$ potassium carbonate
NaCl sodium chloride
KCl potassium chloride
$Na_2HPO_4 \cdot 2H_2O$ disodium hydrogen phosphate dihydrate
μL, μl microlitre
mL, ml millilitre
PE petroleum ether (60-90° C.)
RT, rt, r.t. room temperature
HEPES 4-hydroxyethyl piperazine ethanesulfonic acid
Glucan glucosamine
Saline physiological saline
MTBE methyl tert-butyl ether
HCOOH formic acid
EDTA ethylenediamine tetraacetic acid The following synthetic schemes describe the steps for preparing the compounds disclosed herein, unless otherwise specified, wherein each $R^{1a}$, $R^{1b}$, $R^{1c}$, $R^{1d}$, $R^{1e}$, $R^{2a}$, $R^{2b}$, $R^{2c}$, $R^{3a}$, $R^{3b}$ and $R^u$ is as defined herein.

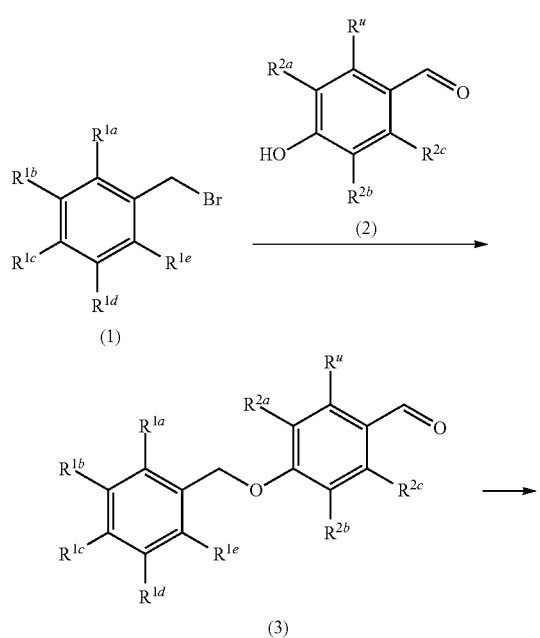

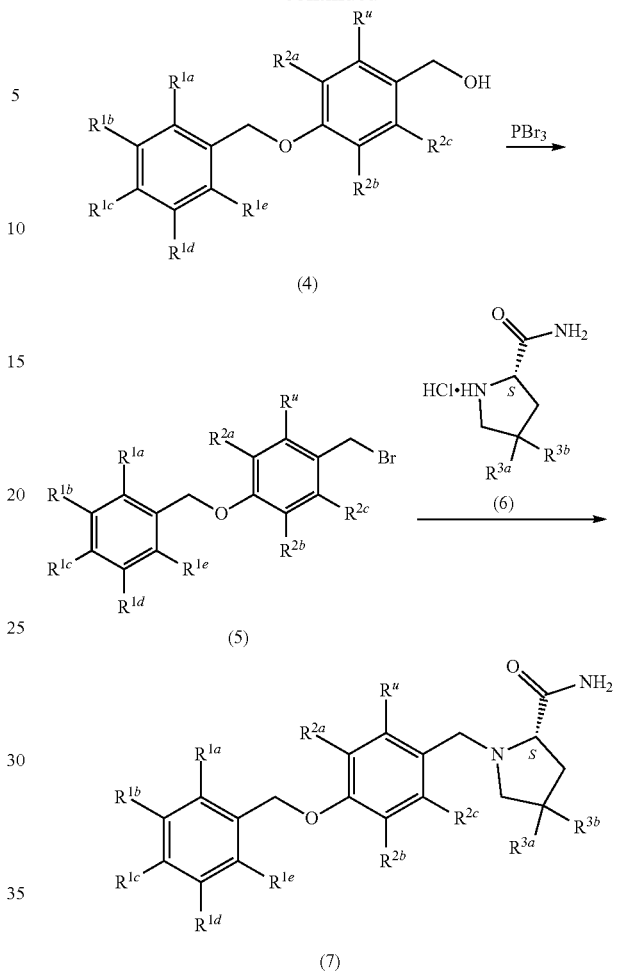

A compound of formula (7) can be prepared through the following process: a compound of formula (1) and a compound of formula (2) can react in the presence of a base to get a compound of formula (3). The compound of formula (3) can be suffered by a reducing agent to get a compound of formula (4). The compound of formula (4) can react with phosphorus tribromide to get a compound of formula (5). The compound of formula (5) can react with a compound of formula (6) to get a compound of formula (7).

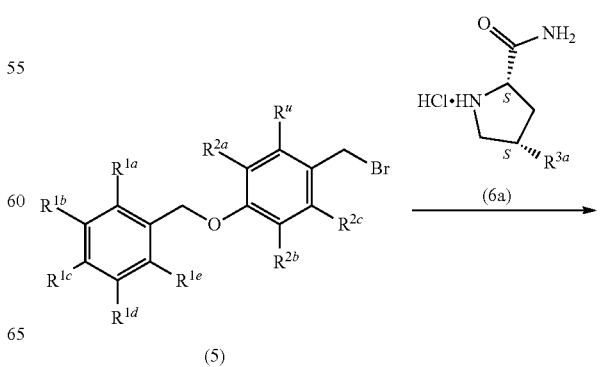

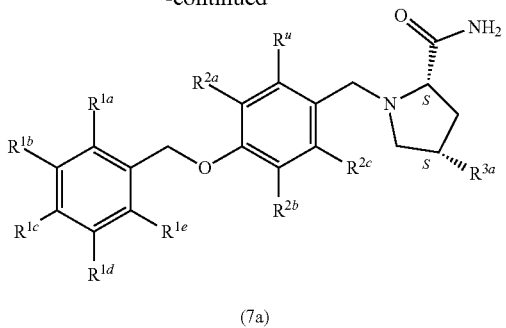

(7a)

A compound of formula (7a) can be prepared through the following process: a compound of formula (5) and a compound of formula (6a) can react to get a compound of formula (7a).

Scheme 3

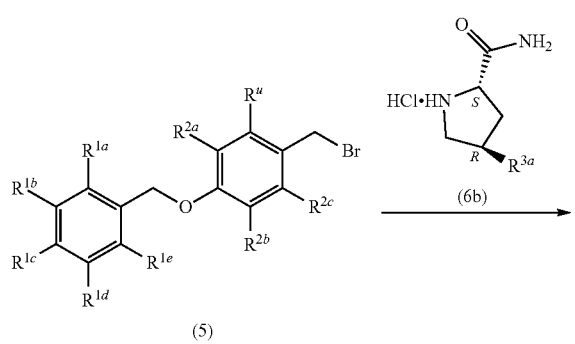

(7b)

A compound of formula (72) can be prepared through the following process: a compound of formula (5) and a compound of formula (6b) can react to get a compound of formula (7b).

The following examples are provided to further illustrate the compounds, pharmaceutical compositions and their applications thereof.

EXAMPLE

Example 1 Synthesis of (2S,4S)-4-fluoro-1-(4-(3-fluorobenzyloxy)benzyl)pyrrolidine-2-formamide

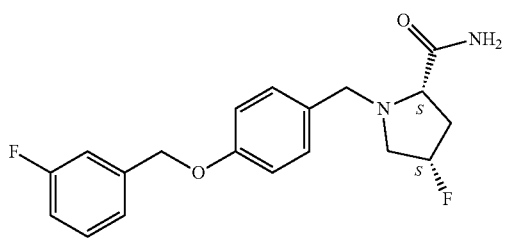

Step 1) Synthesis of 4-(3-fluorobenzyloxy)benzaldehyde

To a 100 mL single-neck round bottom flask were added 4-hydroxybenzaldehyde (1.0 g, 8.19 mmol), 3-fluorobenzyl bromide (1.06 mL, 8.64 mmol), potassium carbonate (4.30 g, 32.76 mmol) and acetone (50 mL) in turn, the mixture was stirred at 60° C. for 5 h and cooled to rt. And then the mixture was filtered, the filtrate was collected and purified on a silica gel column eluted with PE/EtOAc (v/v=10/1) to get the title compound as a white solid (1.78 g, 94.7%).

MS (ESI, pos. ion) m/z: 231.1 [M+H]$^+$;

$^1$H NMR (400 MHz, CDCl$_3$) δ (ppm) 9.89 (s, 1H), 7.85 (d, J=8.8 Hz, 2H), 7.37 (td, J=7.9, 6.0 Hz, 1H), 7.20 (d, J=7.7 Hz, 1H), 7.15 (d, J=9.4 Hz, 1H), 7.08 (s, 1H), 7.06 (s, 1H), 7.03 (dd, J=8.4, 2.2 Hz, 1H), 5.15 (s, 2H).

Step 2) Synthesis of (4-(3-fluorobenzyloxy)phenyl)methanol 4-(3-Fluorobenzoxy)benzaldehyde (1.70 g, 7.39 mmol) was added to a 100 mL single-neck round bottom flask, and then methanol (10 mL) was added, after that the mixture was moved to a low temperature tank at 0° C., sodium borohydride (0.56 g, 14.78 mmol) was added slowly, the mixture was continuously stirred for 1 h After the reaction was completed, the mixture was concentrated to remove methanol, then EtOAc (40 mL) was added, the resulting mixture was washed with water (20 mL×3). The EtOAc phase was collected and concentrated to get the title compound as a white solid (1.69 g, 98.8%).

$^1$H NMR (400 MHz, CDCl$_3$) δ (ppm) 7.35 (dd, J=13.9, 7.9 Hz, 1H), 7.31 (s, 1H), 7.28 (s, 1H), 7.20 (d, J=7.8 Hz, 1H), 7.16 (d, J=9.6 Hz, 1H), 7.01 (td, J=8.5, 1.8 Hz, 1H), 6.96 (s, 1H), 6.94 (s, 1H), 5.07 (s, 2H), 4.61 (d, J=3.8 Hz, 2H).

Step 3) Synthesis of 1-((4-(bromomethyl)phenyloxy)methyl)-3-fluorobenzene (4-(3-Fluorobenzyloxy)phenyl)methanol (1.65 g, 7.11 mmol) and DCM (15 mL) were added into a 50 mL two-neck round bottom flask in turn, and the mixture was moved to a low temperature tank at 0° C., then phosphorus tribromide (1.00 mL, 10.66 mmol) was added slowly. After the addition, the mixture was stirred at rt for 22 h. After the reaction was completed, the mixture was poured into ice water (30 m). The DCM phase was collected and concentrated to get the title compound as a colorless oil (1.98 g, 94.7%) without further purification.

Step 4) Synthesis of (2S,4S)-4-fluoro-1-(4-(3-fluorobenzyloxy)benzyl)pyrrolidine-2-formamide (2S,4S)-4-Fluoropyrrolidine-2-formamide hydrochloride (1.13 g, 6.71 mmol), DCM (20 mL), triethylamine (1.84 mL, 13.22 mmol) and 1-((4-(bromomethyl)phenyloxy)methyl)-3-fluorobenzene (1.98 g, 6.71 mmol) were added to a 100 mL single-neck round bottom flask in turn, the mixture was stirred at rt for 16 h, after the reaction was completed, the mixture was concentrated and purified on a silica gel column eluted with EtOAc to get the title compound as a white solid (0.71 g, 30.6%).

MS (ESI, pos. ion) m/z: 347.10 [M+H]$^+$;
$^1$H NMR (400 MHz, DMSO-d$_6$) δ (ppm) 7.48-7.40 (m, 1H), 7.31-7.25 (m, 2H), 7.21 (s, 1H), 7.18 (d, J=2.9 Hz, 1H), 7.16-7.11 (m, 1H), 6.99 (s, 1H), 6.97 (s, 1H), 5.20-5.05 (m, 1H), 5.12 (s, 2H), 3.82 (d, J=12.8 Hz, 1H), 3.32 (d, J=12.9 Hz, 1H), 3.04-2.96 (m, 2H), 2.60-2.36 (m, 2H), 2.02-1.78 (m, 1H);
$^{13}$C NMR (101 MHz, DMSO-d$_6$) δ (ppm) 175.4, 162.7 (d, J=243.6 Hz), 157.8, 140.6 (d, J=7.4 Hz), 131.0, 130.9 (d, J=1.3 Hz), 130.5, 124.0 (d, J=2.7 Hz), 115.1, 115.0, 114.9, 114.8, 114.5, 92.8 (d, J=174.7 Hz), 68.8, 66.1, 59.3 (d, J=20.9 Hz), 58.0, 37.8 (d, J=22.0 Hz).

Example 2 Synthesis of (2S,4S)-4-fluoro-1-(4-(3-fluorobenzyloxy)-2-methylbenzyl) pyrrolidine-2-formamide

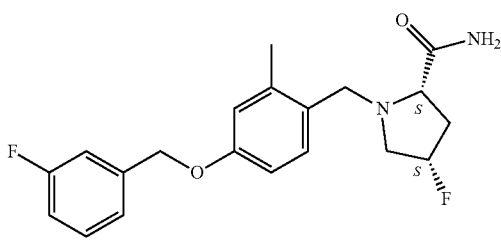

Step 1) Synthesis of 4-(3-fluorobenzyloxy)-2-methylbenzaldehyde

The title compound of this step was prepared by referring to the method described in step 1 of example 1, i.e. 3-fluorobenzyl bromide (0.48 mL, 3.90 mmol), 4-hydroxy-2-methylbenzaldehyde (0.50 g, 3.67 mmol), potassium carbonate (2.03 g, 14.70 mmol) and acetone (35 mL) were added into a 100 mL single-neck round bottom flask in turn to react, and then the mixture was concentrated and purified on a silica gel column eluted with PE/EtOAc (v/v=9/1) to get the title compound as a white solid (0.78 g, 87.0%).

MS (ESI, pos. ion) m/z: 245.1 [M+H]$^+$;
$^1$H NMR (400 MHz, CDCl$_3$) δ (ppm) 10.14 (s, 1H), 7.77 (d, J=8.6 Hz, 1H), 7.37 (tt, J=13.3, 6.7 Hz, 1H), 7.19 (dd, J=18.1, 8.6 Hz, 2H), 7.05 (td, J=8.4, 2.2 Hz, 1H), 6.96-6.87 (m, 1H), 6.87-6.80 (m, 1H), 5.13 (d, J=7.8 Hz, 2H), 2.67 (s, 3H).

Step 2) Synthesis of (4-(3-fluorobenzyloxy)-2-methylphenyl)methanol

The title compound of this step was prepared by referring to the method described in step 2 of example 1, i.e. 4-(3-fluorobenzyloxy)-2-methylbenzaldehyde (0.76 g, 3.11 mmol), methanol (10 ml) and sodium borohydride (0.24 g, 6.22 mmol) were added into a 100 mL single-neck round bottom flask in turn to react to get the title compound as a white solid (0.76 g, 99.2%).

$^1$H NMR (400 MHz, CDCl$_3$) δ (ppm) 7.34 (dd, J=13.9, 7.9 Hz, 1H), 7.30 (s, 1H), 7.28 (s, 1H), 7.19 (d, J=7.8 Hz, 1H), 7.05 (s, 1H), 6.97 (s, 1H), 6.95 (s, 1H), 5.06 (s, 2H), 4.60 (d, J=3.8 Hz, 2H), 2.35 (s, 3H).

Step 3) Synthesis of 1-bromomethyl-4-(3-fluorobenzyloxy)-2-methylbenzene

The title compound of this step was prepared by referring to the method described in step 3 of example 1, i.e. (4-(3-fluorobenzyloxy)-2-methylphenyl)methanol (0.75 g, 3.05 mmol), DCM (10 ml) and phosphorus tribromide (0.43 mL, 4.57 mmol) were added into a 50 mL two-neck round bottom flask in turn to react to get the title compound as a colorless oil (0.91 g, 96.6%).

Step 4) Synthesis of (2S,4S)-4-fluoro-1-(4-(3-fluorobenzyloxy)-2-methylbenzyl)pyrrolidine-2-formamide The title compound of this step was prepared by referring to the method described in step 4 of example 1, i.e. (2S,4S)-4-Fluoropyrrolidine-2-formamide hydrochloride (0.49 g, 2.95 mmol), DCM (15 mL), triethylamine (0.82 mL, 5.90 mmol) and 1-bromomethyl-4-(3-fluorobenzyloxy)-2-methylbenzene (0.91 g, 2.95 mmol) were added to a 100 mL single-neck round bottom flask in turn to react, the mixture was concentrated and purified on a silica gel column eluted with EtOAc to get the title compound as a white solid (0.35 g, 32.9%).

MS (ESI, pos. ion) m/z: 361.2 [M+H]$^+$;
$^1$H NMR (400 MHz, DMSO-d$_6$) δ (ppm) 7.33 (d, J=5.2 Hz, 1H), 7.19-7.17 (m, 1H), 7.12-7.10 (m, 1H), 7.00 (s, 1H), 6.85 (s, 1H), 6.79 (s, 1H), 6.73 (s, 1H), 5.19-5.05 (m, 1H), 5.10 (s, 2H), 3.84 (d, J=12.9 Hz, 1H), 3.30 (d, J=12.8 Hz, 1H), 3.05-2.94 (m, 2H), 2.61-2.36 (m, 2H), 2.03-1.80 (m, 1H), 2.33 (s, 3H);
$^{13}$C NMR (101 MHz, DMSO-d$_6$) δ (ppm) 175.9, 163.0 (d, J=244.1 Hz), 158.0, 140.7 (d, J=7.3 Hz), 137.9, 131.4, 130.2 (d, J=8.1 Hz), 129.0, 123.1 (d, J=3.0 Hz), 117.3, 114.8 (d, J=21.0 Hz), 114.3 (d, J=22.1 Hz), 111.4, 92.6 (d, J=175.0 Hz), 67.8, 66.0, 59.5 (d, J=21.9 Hz), 58.2, 38.2 (d, J=22.2 Hz).

Example 3 Synthesis of (2S,4S)-4-fluoro-1-(2-fluoro-4-(3-fluorobenzyloxy)benzyl)pyrrolidine-2-formamide

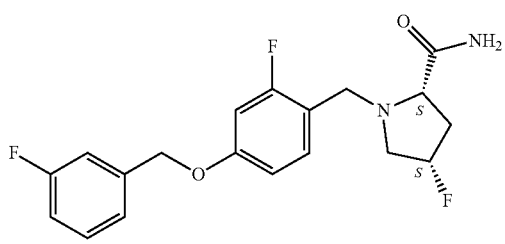

Step 1) Synthesis of 2-fluoro-4-(3-fluorobenzyloxy)benzaldehyde

The title compound of this step was prepared by referring to the method described in step 1 of example 1, i.e. 3-fluorobenzyl bromide (0.46 mL, 3.75 mmol), 2-fluoro-4-hydroxybenzaldehyde (0.50 g, 3.57 mmol), potassium carbonate (1.97 g, 14.28 mmol) and acetone (25 mL) were added into a 100 mL single-neck round bottom flask in turn to react, and then the mixture was concentrated and purified on a silica gel column eluted with PE/EtOAc (v/v=10/1) to get the title compound as a light red solid (0.73 g, 82.4%).

MS (ESI, pos. ion) m/z: 249.1 [M+H]$^+$;
$^1$H NMR (400 MHz, CDCl$_3$) δ (ppm) 10.20 (s, 1H), 7.83 (t, J=8.4 Hz, 1H), 7.37 (td, J=7.9, 5.9 Hz, 1H), 7.18 (d, J=7.6 Hz, 1H), 7.13 (d, J=9.4 Hz, 1H), 7.05 (td, J=8.4, 2.2 Hz, 1H), 6.84 (dd, J=8.8, 2.2 Hz, 1H), 6.70 (dd, J=12.2, 2.3 Hz, 1H), 5.12 (s, 2H).

Step 2) Synthesis of (2-fluoro-4-(3-fluorobenzyloxy)phenyl)methanol

The title compound of this step was prepared by referring to the method described in step 2 of example 1, i.e. 2-fluoro-4-(3-fluorobenzyloxy)benzaldehyde (0.72 g, 2.90 mmol), methanol (10 ml) and sodium borohydride (0.22 g, 5.80 mmol) were added into a 100 mL single-neck round bottom flask in turn to react to get the title compound as a white solid (0.72 g, 99.2%).

$^1$H NMR (400 MHz, CDCl$_3$) δ (ppm) 7.39-7.33 (m, 1H), 7.30 (t, J=8.7 Hz, 1H), 7.18 (d, J=7.7 Hz, 1H), 7.14 (d, J=9.5 Hz, 1H), 7.03 (dd, J=11.6, 5.1 Hz, 1H), 6.74 (dd, J=8.4, 2.1 Hz, 1H), 6.68 (dd, J=11.7, 2.1 Hz, 1H), 5.04 (s, 2H), 4.67 (s, 2H).

Step 3) Synthesis of 1-(bromomethyl)-2-fluoro-4-(3-fluorobenzyloxy)benzene

The title compound of this step was prepared by referring to the method described in step 3 of example 1, i.e. (2-fluoro-4-(3-fluorobenzyloxy)phenyl)methanol (0.71 g, 2.84 mmol), DCM (10 mL) and phosphorus tribromide (0.40 mL, 4.26 mmol) were added into a 50 mL two-neck round bottom flask in turn to react to get the title compound as a light red oil (0.84 g, 94.8%).

Step 4) Synthesis of (2S,4S)-4-fluoro-1-(2-fluoro-4-(3-fluorobenzyloxy)benzyl)pyrrolidine-2-formamide The title compound of this step was prepared by referring to the method described in step 4 of example 1, i.e. (2S,4S)-4-Fluoropyrrolidine-2-formamide hydrochloride (0.45 g, 2.69 mmol), DCM (15 mL), triethylamine (0.75 ML, 5.38 mmol) and 1-(bromomethyl)-2-fluoro-4-(3-fluorobenzyloxy)benzene (0.84 g, 2.69 mmol) were added into a 100 mL single-neck round bottom flask in turn to react, the mixture was concentrated and purified on a silica gel column eluted with EtOAc to get the title compound as a white solid (0.31 g, 31.7%).

MS (ESI, pos. ion) m/z: 365.2 [M+H]$^+$;
$^1$H NMR (600 MHz, DMSO-d$_6$) δ (ppm) 7.44 (dd, J=14.2, 7.7 Hz, 1H), 7.34 (t, J=8.6 Hz, 1H), 7.30-7.26 (m, 2H), 7.16 (t, J=8.6 Hz, 1H), 6.91 (dd, J=12.0, 1.5 Hz, 1H), 6.85 (d, J=8.4 Hz, 1H), 5.13 (s, 2H), 5.12 (dt, J=54.2, 3.7 Hz, 1H), 3.80 (d, J=13.0 Hz, 1H), 3.48 (d, J=13.0 Hz, 1H), 3.11-2.91 (m, 2H), 2.61-2.29 (m, 2H), 1.95-1.87 (m, 1H);

$^{13}$C NMR (151 MHz, DMSO-d$_6$) δ (ppm) 176.6, 162.9 (d, J=246.7 Hz), 161.8 (d, J=246.8 Hz), 159.4 (d, J=11.2 Hz), 138.8 (d, J=7.4 Hz), 131.8 (d, J=6.4 Hz), 130.2 (d, J=8.2 Hz), 122.7 (d, J=2.8 Hz), 116.7 (d, J=15.5 Hz), 115.0 (d, J=21.1 Hz), 114.2 (d, J=22.1 Hz), 110.5 (d, J=2.9 Hz), 102.7 (d, J=25.9 Hz), 92.1 (d, J=177.5 Hz), 69.4 (d, J=1.7 Hz), 65.2, 59.2 (d, J=20.9 Hz), 51.9, 37.9 (d, J=22.7 Hz).

Example 4 Synthesis of (2S,4S)-1-(2-chloro-4-(3-fluorobenzyloxy)benzyl)-4-fluoropyrrolidine-2-formamide

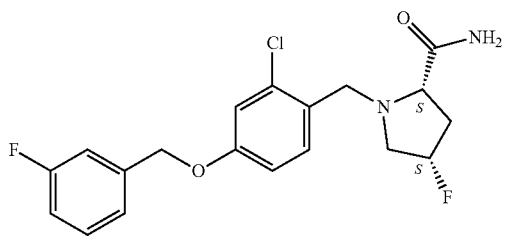

Step 1) Synthesis of 2-chloro-4-(3-fluorobenzyloxy)benzaldehyde

The title compound of this step was prepared by referring to the method described in step 1 of example 1, i.e. 3-fluorobenzyl bromide (1.65 mL, 13.46 mmol), 2-chloro-4-hydroxybenzaldehyde (2.00 g, 12.82 mmol), potassium carbonate (7.07 g, 51.28 mmol) and acetone (50 mL) were added into a 100 mL single-neck round bottom flask in turn to react, and then the mixture was concentrated and purified on a silica gel column eluted with PE/EtOAc (v/v=9/1) to get the title compound as a white solid (2.10 g, 62.2%).

MS (ESI, pos. ion) m/z: 265.1 [M+H]$^+$;
$^1$H NMR (400 MHz, CDCl$_3$) δ (ppm) 10.36 (d, J=0.6 Hz, 1H), 7.92 (t, J=7.1 Hz, 1H), 7.40 (td, J=7.9, 5.9 Hz, 1H), 7.22 (t, J=8.3 Hz, 1H), 7.16 (d, J=9.4 Hz, 1H), 7.08 (td, J=8.4, 2.2 Hz, 1H), 7.03 (d, J=2.4 Hz, 1H), 6.98 (dd, J=8.7, 1.8 Hz, 1H), 5.15 (s, 2H).

Step 2) Synthesis of (2-chloro-4-(3-fluorobenzyloxy)phenyl)methanol

The title compound of this step was prepared by referring to the method described in step 2 of example 1, i.e. 2-chloro-4-(3-fluorobenzyloxy)benzaldehyde (1.45 g, 5.49 mmol), methanol (20 mL) and sodium borohydride (0.42 g, 10.98 mmol) were added into a 100 mL single-neck round bottom flask in turn to react to get the title compound as a white solid (1.45 g, 99.3%).

$^1$H NMR (400 MHz, CDCl$_3$) δ (ppm) 7.40-7.34 (m, 1H), 7.32 (t, J=8.7 Hz, 1H), 7.20 (d, J=7.7 Hz, 1H), 7.16 (d, J=9.5 Hz, 1H), 7.05 (dd, J=11.6, 5.1 Hz, 1H), 6.80 (dd, J=8.4, 2.1 Hz, 1H), 6.54 (dd, J=11.7, 2.1 Hz, 1H), 5.10 (s, 2H), 4.62 (s, 2H).

Step 3) Synthesis of 1-bromomethyl-2-chloro-4-(3-fluorobenzyloxy)benzene

The title compound of this step was prepared by referring to the method described in step 3 of example 1, i.e. (2-chloro-4-(3-fluorobenzyloxy)phenyl)methanol (1.43 g, 5.37 mmol), DCM (15 mL) and phosphorus tribromide (0.75 mL, 8.05 mmol) were added into a 50 mL two-neck round bottom flask in turn to react to get the title compound as a white solid (1.50 g, 85.2%).

Step 4) Synthesis of (2S,4S)-1-(2-chloro-4-(3-fluorobenzyloxy)benzyl)-4-fluoropyrrolidine-2-formamide The title compound of this step was prepared by referring to the method described in step 4 of example 1, i.e. (2S, 4S)-4-fluoropyrrolidine-2-formamide hydrochloride (0.77 g, 4.57 mmol), DCM (15 mL), triethylamine (1.27 mL, 9.14 mmol) and 1-bromomethyl-2-chloro-4-(3-fluorobenzyloxy)benzene (1.50 g, 4.57 mmol) were added to a 100 mL single-neck round bottom flask in turn to react, the mixture was concentrated and purified on a silica gel column eluted with EtOAc to get the title compound as a white solid (0.51 g, 29.4%).

MS (ESI, pos. ion) m/z: 381.2 [M+H]$^+$;

$^1$H NMR (400 MHz, DMSO-d$_6$) δ (ppm) 7.46-7.39 (m, 1H), 7.38 (d, J=8.4 Hz, 2H), 7.24-7.15 (m, 1H), 7.13 (d, J=2.5 Hz, 1H), 7.01 (dd, J=8.6, 2.5 Hz, 1H), 6.95 (s, 1H), 5.20-5.06 (m, 1H), 5.11 (s, 2H), 3.83 (d, J=12.8 Hz, 1H), 3.32 (d, J=12.9 Hz, 1H), 3.06-2.97 (m, 2H), 2.60-2.38 (m, 2H), 2.03-1.80 (m, 1H);

$^{13}$C NMR (151 MHz, DMSO-d$_6$) δ (ppm) 174.6, 162.3 (d, J=244.2 Hz), 159.1, 142.1 (d, J=7.5 Hz), 136.7, 131.4, 130.7 (d, J=8.1 Hz), 128.4, 124.5 (d, J=2.7 Hz), 115.6, 115.0 (d, J=21.1 Hz), 114.4 (d, J=21.0 Hz), 114.1, 92.6 (d, J=174.8 Hz), 69.0, 66.2, 59.5 (d, J=21.9 Hz), 58.7, 37.9 (d, J=22.1 Hz).

Example 5 Synthesis of (2S,4S)-1-(4-(3-chlorobenzyloxy)benzyl)-4-fluoropyrrolidine-2-formamide

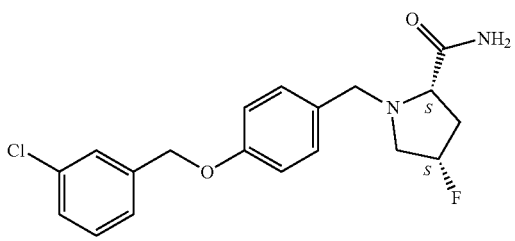

Step 1) Synthesis of 4-(3-chlorobenzyloxy)benzaldehyde

The title compound of this step was prepared by referring to the method described in step 1 of example 1, i.e. 3-chlorobenzyl bromide (1.40 mL, 10.76 mmol), 4-hydroxybenzaldehyde (1.25 g, 10.25 mmol), potassium carbonate (5.66 g, 41.00 mmol) and acetone (50 mL) were added into a 100 mL single-neck round bottom flask in turn to react, and then the mixture was concentrated and purified on a silica gel column eluted with PE/DCM (v/v=1/1) to get the title compound as a white solid (2.42 g, 96.0%).

MS (ESI, pos. ion) m/z: 247.1 [M+H]$^+$;

$^1$H NMR (400 MHz, CDCl$_3$) δ (ppm) 9.88 (s, 1H), 7.84 (d, J=8.7 Hz, 2H), 7.43 (s, 1H), 7.33-7.31 (m, 3H), 7.06 (d, J=8.6 Hz, 2H), 5.11 (s, 2H).

Step 2) Synthesis of (4-(3-chlorobenzyloxy)phenyl)methanol

The title compound of this step was prepared by referring to the method described in step 2 of example 1, i.e. 4-(3-chlorobenzyloxy)benzaldehyde (1.25 g, 5.08 mmol), methanol (15 mL) and sodium borohydride (0.39 g, 10.16 mmol) were added into a 100 mL single-neck round bottom flask in turn to react to get the title compound as a white solid (1.25 g, 99.2%).

$^1$H NMR (400 MHz, CDCl$_3$) δ (ppm) 7.82 (d, J=8.8 Hz, 2H), 7.45 (s, 1H), 7.35-7.32 (m, 3H), 7.08 (d, J=8.7 Hz, 2H), 5.10 (s, 2H), 4.63 (s, 2H).

Step 3) Synthesis of 1-((4-(bromomethyl)phenyloxy)methyl)-3-chlorobenzene

The title compound of this step was prepared by referring to the method described in step 3 of example 1, i.e. (4-(3-chlorobenzyloxy)phenyl)methanol (1.23 g, 4.96 mmol), DCM (15 mL) and phosphorus tribromide (0.70 mL, 7.44 mmol) were added into a 50 mL two-neck round bottom flask in turn to react to get the title compound as a colorless oil (1.28 g, 83.1%).

Step 4) Synthesis of (2S,4S)-1-(4-(3-chlorobenzyloxy)benzyl)-4-fluoropyrrolidine-2-formamide The title compound of this step was prepared by referring to the method described in step 4 of example 1, i.e. (2S, 4S)-4-fluoropyrrolidine-2-formamide hydrochloride (0.69 g, 4.13 mmol), DCM (15 mL), triethylamine (1.15 ML, 8.26 mmol) and 1-((4-(bromomethyl)phenyloxy)methyl)-3-chlorobenzene (1.28 g, 4.13 mmol) were added into a 100 mL single-neck round bottom flask in turn to react, the mixture was concentrated and purified on a silica gel column eluted with EtOAc to get the title compound as a white solid (0.50 g, 33.5%).

MS (ESI, pos. ion) m/z: 363.2 [M+H]$^+$; H NMR (400 MHz, DMSO-d$_6$) δ (ppm) 7.53-7.42 (m, 1H), 7.37-7.28 (m, 2H), 7.25-7.21 (m, 3H), 7.04 (d, J=8.4 Hz, 2H), 5.20-5.05 (m, 1H), 5.12 (s, 2H), 3.84 (d, J=12.9 Hz, 1H), 3.30 (d, J=13.0 Hz, 1H), 3.07-2.98 (m, 2H), 2.62-2.37 (m, 2H), 2.04-1.82 (m, 1H);

$^{13}$C NMR (101 MHz, DMSO-d$_6$) δ (ppm) 174.2, 163.1, 158.8, 142.8, 130.8, 130.1, 129.6, 125.7, 116.2, 115.7, 115.2, 114.5, 114.0, 92.8 (d, J=175.0 Hz), 69.2, 66.5, 59.2 (d, J=22.0 Hz), 58.8, 38.2 (d, J=22.0 Hz).

Example 6 Synthesis of (2S,4S)-1-(4-(3-bromobenzyloxy)benzyl)-4-fluoropyrrolidine-2-formamide

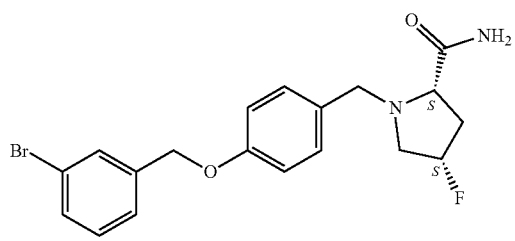

Step 1) Synthesis of 4-(3-bromobenzyloxy)benzaldehyde

The title compound of this step was prepared by referring to the method described in step 1 of example 1, i.e. 3-bromobenzyl bromide (1.40 mL, 8.61 mmol), 4-hydroxybenzaldehyde (1.00 g, 8.20 mmol), potassium carbonate (4.46 g, 32.80 mmol) and acetone (20 mL) were added into a 100 mL single-neck round bottom flask in turn to react, and then the mixture was concentrated and purified on a silica gel column eluted with PE/DCM (v/v=1/1) to get the title compound as a white solid (2.31 g, 97.1%).

MS (ESI, pos. ion) m/z: 291.1 [M+H]+;

$^1$H NMR (400 MHz, CDCl$_3$) δ (ppm) 9.87 (s, 1H), 7.83 (d, J=8.7 Hz, 2H), 7.46 (s, 1H), 7.37-7.32 (m, 3H), 7.10 (d, J=8.6 Hz, 2H), 5.12 (s, 2H).

Step 2) Synthesis of (4-(3-bromobenzyloxy)phenyl)methanol

The title compound of this step was prepared by referring to the method described in step 2 of example 1, i.e. 4-(3-bromobenzyloxy)benzaldehyde (1.50 g, 5.17 mmol), methanol (20 mL) and sodium borohydride (0.39 g, 10.34 mmol) were added into a 100 mL single-neck round bottom flask in turn to react to get the title compound as a light yellow solid (1.49 g, 98.7%).

$^1$H NMR (400 MHz, CDCl$_3$) δ (ppm) 7.84 (d, J=8.7 Hz, 2H), 7.45 (s, 1H), 7.38-7.33 (m, 3H), 7.12 (d, J=8.7 Hz, 2H), 5.10 (s, 2H), 4.62 (s, 2H).

Step 3) Synthesis of 1-bromo-3-((4-(bromomethyl)phenyloxy)methyl)benzene

The title compound of this step was prepared by referring to the method described in step 3 of example 1, i.e. (4-(3-bromobenzyloxy)phenyl)methanol (1.49 g, 5.03 mmol), DCM (15 mL) and phosphorus tribromide (0.95 mL, 10.06 mmol) were added into a 50 mL two-neck round bottom flask in turn to react to get the title compound as a colorless oil (1.56 g, 86.7%).

Step 4) Synthesis of (2S,4S)-1-(4-(3-bromobenzyloxy)benzyl)-4-fluoropyrrolidine-2-formamide The title compound of this step was prepared by referring to the method described in step 4 of example 1, i.e. (2S,4S)-4-fluoropyrrolidine-2-formamide hydrochloride (0.74 g, 4.41 mmol), DCM (15 ML), triethylamine (1.15 mL, 8.82 mmol) and 1-bromo-3-((4-(bromomethyl)phenyloxy)methyl)benzene (1.56 g, 4.41 mmol) were added into a 100 mL single-neck round bottom flask in turn to react, the mixture was concentrated and purified on a silica gel column eluted with EtOAc to get the title compound as a white solid (0.58 g, 32.4%).

MS (ESI, pos. ion) m/z: 407.1 [M+H]+;

$^1$H NMR (400 MHz, DMSO-d$_6$) δ (ppm) 7.52-7.41 (m, 1H), 7.40-7.32 (m, 2H), 7.28-7.22 (m, 3H), 7.08 (d, J=8.4 Hz, 2H), 5.21-5.04 (m, 1H), 5.13 (s, 2H), 3.85 (d, J=12.8 Hz, 1H), 3.32 (d, J=13.1 Hz, 1H), 3.08-3.00 (m, 2H), 2.63-2.34 (m, 2H), 2.05-1.83 (m, 1H);

$^{13}$C NMR (101 MHz, DMSO-d$_6$) δ (ppm) 174.1, 163.2, 159.0, 140.5, 130.8, 130.3, 129.9, 125.7, 116.3, 115.6, 115.0, 114.4, 114.0, 92.4 (d, J=175.1 Hz), 69.3, 66.5, 59.3 (d, J=22.1 Hz), 58.9, 38.3 (d, J=22.0 Hz).

Example 7 Synthesis of (2S,4S)-4-fluoro-1-(4-(3-methylbenzyloxy)benzyl)pyrrolidine-2-formamide

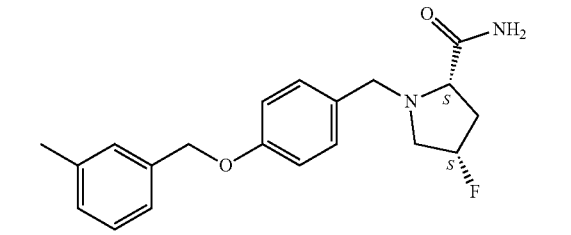

Step 1) Synthesis of 4-(3-methylbenzyloxy)benzaldehyde

The title compound of this step was prepared by referring to the method described in step 1 of example 1, i.e. 3-methylbenzyl bromide (1.20 mL, 8.61 mmol), 4-hydroxybenzaldehyde (1.00 g, 8.20 mmol), potassium carbonate (4.46 g, 32.80 mmol) and acetone (20 mL) were added into a 100 mL single-neck round bottom flask in turn to react, and then the mixture was concentrated and purified on a silica gel column eluted with PE/DCM (v/v=1/1) to get the title compound as a colorless oil (1.84 g, 99.4%).

MS (ESI, pos. ion) m/z: 227.2 [M+H]+;

$^1$H NMR (400 MHz, CDCl$_3$) δ (ppm) 9.89 (s, 1H), 7.49 (d, J=8.7 Hz, 2H), 7.30 (t, J=7.5 Hz, 1H), 7.25-7.20 (m, 2H), 7.17 (d, J=7.4 Hz, 1H), 7.08 (d, J=8.7 Hz, 2H), 5.11 (s, 2H), 2.38 (s, 3H).

Step 2) Synthesis of (4-(3-methylbenzyloxy)phenyl)methanol

The title compound of this step was prepared by referring to the method described in step 2 of example 1, i.e. 4-(3-methylbenzyloxy)benzaldehyde (1.50 g, 6.64 mmol), methanol (20 mL) and sodium borohydride (0.50 g, 13.28 mmol) were added into a 100 mL single-neck round bottom flask in turn to react to get the title compound as a colorless oil (1.50 g, 99.3%).

$^1$H NMR (400 MHz, CDCl$_3$) δ (ppm) 7.48 (d, J=8.6 Hz, 2H), 7.32 (t, J=7.6 Hz, 1H), 7.26-7.22 (m, 2H), 7.18 (d, J=7.4 Hz, 1H), 7.10 (d, J=8.7 Hz, 2H), 5.11 (s, 2H), 4.63 (s, 2H), 2.37 (s, 3H).

Step 3) Synthesis of 1-((4-(bromomethyl)phenyloxy)methyl)-3-methylbenzene

The title compound of this step was prepared by referring to the method described in step 3 of example 1, i.e. (4-(3-methylbenzyloxy)-phenyl)methanol (1.48 g, 6.49 mmol), DCM (15 mL) and phosphorus tribromide (0.90 mL, 9.74 mmol) were added into a 50 mL two-neck round bottom flask in turn to react to get the title compound as a colorless oil (1.70 g, 89.9%).

Step 4) Synthesis of (2S,4S)-4-fluoro-1-(4-(3-methylbenzyloxy)benzyl)pyrrolidine-2-formamide The title compound of this step was prepared by referring to the method described in step 4 of example 1, i.e. (2S,4S)-4-fluoropyrrolidine-2-formamide hydrochloride (0.99 g, 5.87 mmol), DCM (15 mL), triethylamine (1.63 mL, 11.74 mmol) and 1-((4-(bromomethyl)phenyloxy)methyl)-3-methylbenzene (1.70 g, 5.87 mmol) were added into a 100 mL single-neck round bottom flask in turn to react, the mixture was concentrated and purified on a silica gel column eluted with EtOAc to get the title compound as a white solid (0.59 g, 29.5%).

MS (ESI, pos. ion) m/z: 343.1 [M+H]$^+$;

$^1$H NMR (400 MHz, DMSO-d$_6$) δ (ppm) 7.53-7.42 (m, 1H), 7.40-7.33 (m, 2H), 7.30-7.23 (m, 3H), 7.10-7.04 (m, 2H), 5.20-5.05 (m, 1H), 5.10 (s, 2H), 3.86 (d, J=12.8 Hz, 1H), 3.33 (d, J=13.1 Hz, 1H), 3.10-3.02 (m, 2H), 2.64-2.33 (m, 2H), 2.06-1.85 (m, 1H), 2.30 (s, 3H);

$^{13}$C NMR (101 MHz, DMSO-d$_6$) δ (ppm) 174.1, 162.3, 159.0, 141.7, 130.9, 130.3, 129.8, 125.6, 116.5, 115.7, 115.0, 114.8, 114.2, 92.5 (d, J=175.3 Hz), 69.4, 66.7, 59.4 (d, J=22.1 Hz), 59.0, 38.5 (d, J=22.0 Hz).

Example 8 Synthesis of (S)-1-(4-(3-fluorobenzyloxy)benzyl)-4,4-dimethylpyrrolidine-2-formamide

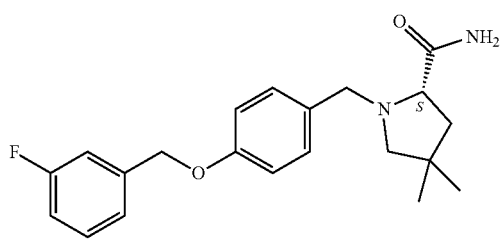

The title compound of this step was prepared by referring to the method described in step 4 of example 1, i.e. (S)-4,4-dimethylpyrrolidine-2-formamide hydrochloride (1.16 g, 6.53 mmol), DCM (20 mL), triethylamine (1.81 mL, 13.06 mmol) and 1-((4-(bromomethyl)phenyloxy)methyl)-3-fluorobenzene (1.92 g, 6.53 mmol) were added into a 100 mL single-neck round bottom flask in turn to react, the mixture was concentrated and purified on a silica gel column eluted with EtOAc to get the title compound as a white solid (0.49 g, 21.1%).

MS (ESI, pos. ion) m/z: 357.1 [M+H]$^+$;

$^1$H NMR (600 MHz, DMSO-d$_6$) δ (ppm) 7.43 (s, 1H), 7.27 (s, 2H), 7.23 (s, 1H), 7.12 (s, 2H), 6.96 (s, 2H), 5.10 (s, 2H), 3.77 (d, J=12.5 Hz, 1H), 3.23 (d, J=12.6 Hz, 1H), 3.02 (s, 1H), 2.55 (d, J=5.0 Hz, 1H), 2.03 (d, J=5.5 Hz, 1H), 1.89 (d, J=10.2 Hz, 1H), 1.55 (d, J=5.7 Hz, 1H), 1.03 (s, 3H), 0.95 (s, 3H);

$^{13}$C NMR (101 MHz, DMSO-d$_6$) δ (ppm) 176.1, 162.7 (d, J=243.6 Hz), 157.6, 140.6 (d, J=7.3 Hz), 131.6, 130.9 (d, J=8.3 Hz), 130.2, 123.9, 115.1, 115.0, 114.9, 114.7, 114.5, 68.8, 67.8, 66.7, 58.6, 45.0, 37.2, 29.4, 28.3.

Example 9 Synthesis of (S)-1-(2-fluoro-4-(3-fluorobenzyloxy)benzyl)-4,4-dimethylpyrrolidine-2-formamide

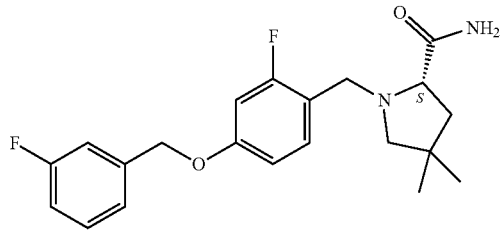

The title compound of this step was prepared by referring to the method described in step 4 of example 1, i.e. (S)-4,4-dimethylpyrrolidine-2-formamide hydrochloride (1.08 g, 6.09 mmol), DCM (20 mL), triethylamine (1.70 mL, 12.18 mmol) and 1-(bromomethyl)-2-fluoro-4-(3-fluorobenzyloxy)benzene (1.90 g, 6.09 mmol) were added into a 100 mL single-neck round bottom flask in turn to react, the mixture was concentrated and purified on a silica gel column eluted with EtOAc to get the title compound as a white solid (0.54 g, 23.8%).

MS (ESI, pos. ion) m/z: 375.2 [M+H]$^+$;

$^1$H NMR (600 MHz, DMSO-d$_6$) δ (ppm) 7.43 (s, 1H), 7.34 (s, 1H), 7.28 (s, 2H), 7.18 (s, 1H), 6.89 (d, J=11.5 Hz, 1H), 6.83 (s, 1H), 5.13 (s, 2H), 3.76 (d, J=12.5 Hz, 1H), 3.40 (s, 1H), 3.04 (s, 1H), 2.54 (s, 1H), 2.14 (s, 1H), 1.90 (t, J=10.3 Hz, 1H), 1.60-1.50 (m, 1H), 1.01 (s, 3H), 0.95 (s, 3H);

$^{13}$C NMR (101 MHz, DMSO-d$_6$) δ (ppm) 176.0, 162.7 (d, J=244.7 Hz), 161.6 (d, J=245.0 Hz), 159.1 (d, J=11.2 Hz), 140.1 (d, J=7.5 Hz), 132.6 (d, J=6.7 Hz), 130.9 (d, J=8.3 Hz), 124.0 (d, J=2.6 Hz), 117.7 (d, J=15.2 Hz), 115.1 (d, J=20.9 Hz), 114.7 (d, J=21.8 Hz), 111.3 (d, J=2.4 Hz), 102.7 (d, J=26.1 Hz), 69.2, 67.4, 66.6, 51.9, 44.9, 37.2, 29.1, 28.0.

Example 10 Synthesis of (S)-4,4-difluoro-1-(4-(3-fluorobenzyloxy)benzyl)pyrrolidine-2-formamide

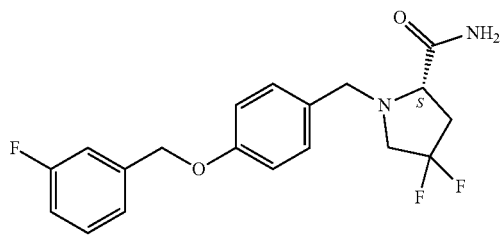

The title compound of this step was prepared by referring to the method described in step 4 of example 1, i.e. (S)-4,4-difluoropyrrolidine-2-formamide hydrochloride (0.76 g, 4.08 mmol), DCM (20 mL), triethylamine (1.13 mL, 8.16 mmol) and 1-((4-(bromomethyl)phenyloxy)methyl)-3-fluorobenzene (1.20 g, 4.08 mmol) were added into a 100 mL single-neck round bottom flask in turn to react, the mixture was concentrated and purified on a silica gel column eluted with EtOAc to get the title compound as a white solid (0.45 g, 30.4%).

MS (ESI, pos. ion) m/z: 365.1 [M+H]$^+$; H NMR (600 MHz, DMSO-d$_6$) δ (ppm) 7.46-7.41 (m, 2H), 7.29-7.26 (m, 3H), 7.15 (t, J=8.2 Hz, 1H), 6.97 (d, J=8.2 Hz, 2H), 5.11 (s, 2H), 3.78-3.76 (m, 1H), 3.43-3.40 (m, 1H), 3.32-3.28 (m, 1H), 3.17-3.16 (m, 1H), 2.74-2.67 (m, 1H), 2.61-2.58 (m, 1H), 2.30-2.19 (m, 1H);

$^{13}$C NMR (151 MHz, DMSO-d$_6$) δ (ppm) 174.6, 162.8 (d, J=246.2 Hz), 158.0, 139.3 (d, J=7.3 Hz), 130.0 (d, J=8.2 Hz), 129.8, 129.0, 127.2 (t, J=249.2 Hz), 122.6 (d, J=2.8 Hz), 114.9, 114.7 (d, J=21.1 Hz), 114.0 (d, J=22.1 Hz), 69.1 (d, J=1.6 Hz), 64.9, 59.3 (t, J=28.4 Hz), 58.3, 46.0.

Example 11 Synthesis of (S)-4,4-difluoro-1-(2-fluoro-4-(3-fluorobenzyloxy)benzyl) pyrrolidine-2-formamide

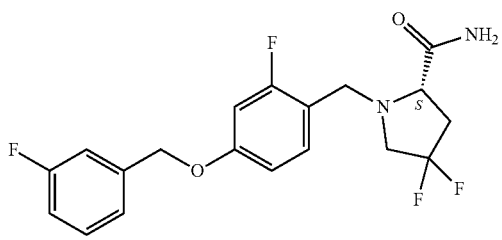

The title compound of this step was prepared by referring to the method described in step 4 of example 1, i.e. (S)-4,4-difluoropyrrolidine-2-formamide hydrochloride (0.59 g, 3.20 mmol), DCM (20 mL), triethylamine (0.89 ML, 6.40 mmol) and 1-(bromomethyl)-2-fluoro-4-(3-fluorobenzyloxy)benzene (1.00 g, 3.20 mmol) were added into a 100 mL single-neck round bottom flask in turn to react, the mixture was concentrated and purified on a silica gel column eluted with EtOAc to get the title compound as a white solid (0.24 g, 19.7%).

MS (ESI, pos. ion) m/z: 383.2 [M+H]$^+$;

$^1$H NMR (400 MHz, DMSO-d$_6$) δ (ppm) 7.44 (dd, J=14.1, 7.9 Hz, 1H), 7.34-7.28 (m, 3H), 7.16 (t, J=7.7 Hz, 1H), 6.94-6.88 (m, 1H), 6.88-6.81 (m, 1H), 5.13 (s, 2H), 3.78 (d, J=13.2 Hz, 1H), 3.57 (d, J=13.2 Hz, 1H), 3.31 (d, J=8.0 Hz, 1H), 3.27-3.10 (m, 1H), 2.78 (dd, J=26.6, 15.3 Hz, 1H), 2.64-2.50 (m, 1H), 2.25-2.20 (m, 1H);

$^{13}$C NMR (101 MHz, DMSO-d$_6$) δ (ppm) 173.2, 162.7 (d, J=244.6 Hz), 161.6 (d, J=245.4 Hz), 159.4 (d, J=11.2 Hz), 140.0 (d, J=7.5 Hz), 132.7 (d, J=6.4 Hz), 131.0 (d, J=8.3 Hz), 129.0 (t, J=247.2 Hz), 124.1 (d, J=2.7 Hz), 116.4 (d, J=15.4 Hz), 115.2 (d, J=20.9 Hz), 114.8 (d, J=21.8 Hz), 111.5 (d, J=2.7 Hz), 102.8 (d, J=25.9 Hz), 69.2, 64.5, 61.6, 59.4 (t, J=28.3 Hz), 50.1.

Example 12 Synthesis of (2S,4R)-4-fluoro-1-(4-(3-fluorobenzyloxy)benzyl)pyrrolidine-2-formamide

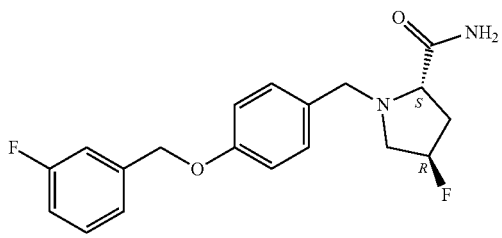

The title compound of this step was prepared by referring to the method described in step 4 of example 1, i.e. (2S,4R)-4-fluoropyrrolidine-2-formamide hydrochloride (0.97 g, 5.81 mmol), DCM (20 mL), triethylamine (1.61 mL, 11.62 mmol) and 1-((4-(bromomethyl)phenyloxy)methyl)-3-fluorobenzene (1.71 g, 5.81 mmol) were added into a 100 mL single-neck round bottom flask in turn to react, the mixture was concentrated and purified on a silica gel column eluted with EtOAc to get the title compound as a white solid (0.87 g, 43.5%).

MS (ESI, pos. ion) m/z: 347.2 [M+H]$^+$;

$^1$H NMR (400 MHz, DMSO-d$_6$) δ (ppm) 7.43 (s, 1H), 7.35 (s, 1H), 7.29-7.27 (m, 2H), 7.16 (s, 2H), 6.96 (d, J=6.6 Hz, 2H), 5.26 (s, 1H), 5.11 (s, 2H), 3.78 (d, J=12.6 Hz, 1H), 3.47 (d, J=12.7 Hz, 1H), 3.29 (s, 1H), 3.23-3.04 (m, 1H), 2.60-2.57 (m, 1H), 2.21 (d, J=16.1 Hz, 1H), 2.00 (d, J=34.1 Hz, 1H);

$^{13}$C NMR (101 MHz, DMSO-d$_6$) δ (ppm) 174.8, 162.7 (d, J=243.6 Hz), 157.7, 140.6 (d, J=7.4 Hz), 131.4, 130.9 (d, J=8.3 Hz), 130.3, 123.9 (d, J=2.6 Hz), 115.1, 115.0, 114.9, 114.7, 114.5, 93.6 (d, J=173.0 Hz), 68.8, 66.0, 58.9 (d, J=22.2 Hz), 57.9, 38.1 (d, J=21.4 Hz).

Example 13 Synthesis of (2S,4R)-4-fluoro-1-(2-fluoro-4-(3-fluorobenzyloxy)benzyl) pyrrolidine-2-formamide

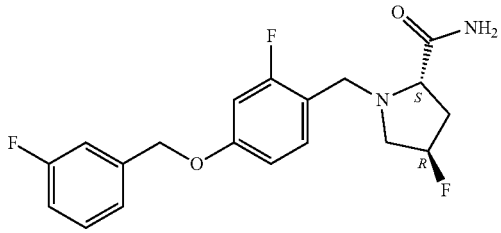

The title compound of this step was prepared by referring to the method described in step 4 of example 1, i.e. (2S,4R)-4-fluoropyrrolidine-2-formamide hydrochloride (0.81 g, 4.81 mmol), DCM (20 mL), triethylamine (1.34 ML, 9.62 mmol) and 1-bromomethyl-2-fluoro-4-(3-fluorobenzyloxy)benzene (1.50 g, 4.81 mmol) were added into a 100 mL single-neck round bottom flask in turn to react, the mixture was concentrated and purified on a silica gel column eluted with EtOAc to get the title compound as a white solid (0.70 g, 40.2%).

MS (ESI, pos. ion) m/z: 365.2 [M+H]$^+$; H NMR (400 MHz, DMSO-d$_6$) δ (ppm) 7.48-7.40 (m, 1H), 7.36 (t, J=8.5 Hz, 1H), 7.30 (s, 1H), 7.19 (s, 1H), 7.16 (d, J=8.2 Hz, 1H), 6.89 (d, J=12.1 Hz, 1H), 6.84 (d, J=8.3 Hz, 1H), 5.25 (s, 1H), 5.13 (s, 2H), 3.76 (d, J=13.2 Hz, 1H), 3.60 (d, J=13.2 Hz, 1H), 3.32-3.26 (m, 1H), 3.25-3.12 (m, 1H), 2.62 (dd, J=30.4, 11.8 Hz, 1H), 2.30-2.12 (m, 1H), 2.08-1.85 (m, 1H);

$^{13}$C NMR (101 MHz, DMSO-d$_6$) δ (ppm) 174.7, 162.7 (d, J=244.6 Hz), 161.5 (d, J=245.2 Hz), 159.1 (d, J=11.2 Hz), 140.1 (d, J=7.5 Hz), 132.5 (d, J=6.5 Hz), 131.0 (d, J=8.3 Hz), 124.1 (d, J=2.6 Hz), 117.5 (d, J=15.2 Hz), 115.2 (d, J=20.9 Hz), 114.8 (d, J=21.8 Hz), 111.3 (d, J=2.6 Hz), 102.7 (d, J=25.9 Hz), 93.5 (d, J=173.1 Hz), 69.2, 65.7, 58.8 (d, J=22.2 Hz), 51.1, 38.1 (d, J=21.3 Hz).

Example 14 Synthesis of (2S,4S)-1-(4-(3-fluorobenzyloxy)benzyl)-4-methylpyrrolidine-2-formamide

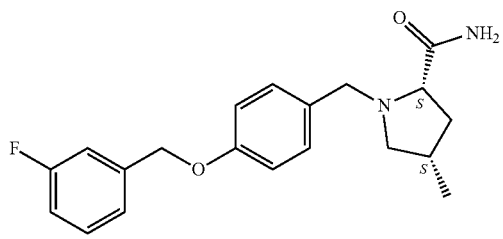

The title compound of this step was prepared by referring to the method described in step 4 of example 1, i.e. (2S,4S)-4-methylpyrrolidine-2-formamide hydrochloride (0.55 g, 3.37 mmol), DCM (15 mL), triethylamine (1.56 mL, 11.24 mmol) and 1-((4-(bromomethyl)phenyloxy)methyl)-3-fluorobenzene (0.83 g, 2.81 mmol) were added into a 100 mL single-neck round bottom flask in turn to react, the mixture was concentrated and purified on a silica gel column eluted with EtOAc to get the title compound as a white solid (0.48 g, 50.2%).

MS (ESI, pos. ion) m/z: 343.2 [M+H]$^+$;

$^1$H NMR (400 MHz, CDCl$_3$) δ (ppm) 7.33 (s, 1H), 7.20 (s, 3H), 7.01-6.94 (m, 3H), 6.49 (s, 1H), 5.04 (s, 2H), 3.87 (d, J=12.4 Hz, 1H), 3.39 (d, J=12.4 Hz, 1H), 3.20 (s, 1H), 2.66 (s, 1H), 2.57 (s, 1H), 2.47 (s, 1H), 2.24 (s, 1H), 1.53 (s, 1H), 1.03 (d, J=3.5 Hz, 3H);

$^{13}$C NMR (101 MHz, CDCl$_3$) δ (ppm) 177.9, 162.8 (d, J=246.2 Hz), 157.6, 139.6 (d, J=7.3 Hz), 131.3, 129.9 (d, J=8.2 Hz), 129.5, 122.5 (d, J=2.9 Hz), 114.7, 114.6, 114.5, 114.1, 113.9, 69.1 (d, J=1.6 Hz), 68.3, 60.3, 59.0, 39.0, 31.6, 20.2.

Example 15 Synthesis of (2S,4S)-1-(2-fluoro-4-(3-fluorobenzyloxy)benzyl)-4-methylpyrrolidine-2-formamide

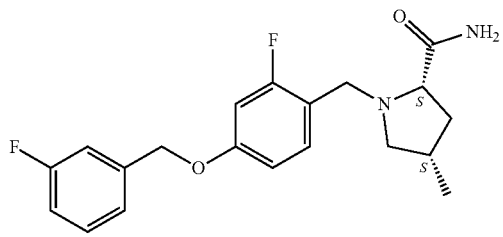

The title compound of this step was prepared by referring to the method described in step 4 of example 1, i.e. (2S,4S)-4-methylpyrrolidine-2-formamide hydrochloride (0.36 g, 2.18 mmol), DCM (10 mL), triethylamine (1.01 mL, 7.28 mmol) and 1-(bromomethyl)-2-fluoro-4-(3-fluorobenzyloxy)benzene (0.57 g, 1.82 mmol) were added into a 100 mL single-neck round bottom flask in turn to react, the mixture was concentrated and purified on a silica gel column eluted with PE/EtOAc (v/v=1/5) to get the title compound as a white solid (0.32 g, 49.1%).

MS (ESI, pos. ion) m/z: 361.3 [M+H]$^+$;

$^1$H NMR (400 MHz, CDCl$_3$) δ (ppm) 7.34 (s, 2H), 7.15 (s, 2H), 7.01 (s, 1H), 6.71-6.66 (m, 2H), 5.02 (s, 2H), 3.90 (d, J=12.6 Hz, 1H), 3.39 (d, J=12.6 Hz, 1H), 3.16 (t, J=7.4 Hz, 1H), 2.59 (s, 2H), 2.50-2.30 (m, 1H), 2.22 (d, J=4.3 Hz, 1H), 1.58-1.39 (m, 1H), 1.00 (d, J=6.0 Hz, 3H);

$^{13}$C NMR (101 MHz, CDCl$_3$) δ (ppm) 177.7, 163.0 (d, J=247.4 Hz), 161.2 (d, J=247.2 Hz), 159.2 (d, J=11.2 Hz), 139.0 (d, J=7.3 Hz), 131.7 (d, J=6.7 Hz), 130.2 (d, J=8.2 Hz), 122.7 (d, J=2.9 Hz), 118.1 (d, J=15.2 Hz), 115.0 (d, J=21.1 Hz), 114.2 (d, J=22.1 Hz), 110.4 (d, J=3.0 Hz), 102.8 (d, J=26.0 Hz), 69.5 (d, J=1.7 Hz), 68.1, 60.4, 53.2, 39.1, 31.6.

BIOLOGICAL ASSAY

Example A1: Evaluation of the Inhibitory Effect of the Compound of the Invention on the Activity of Monoamine Oxidase B Test Method:

Human recombinant monoamine oxidase B expressed in Sf9 cells was used in the test system. In the experiment, firstly, the recombinant monoamine oxidase B was dissolved in the pre-configured HEPES buffer (0.8% NaCl, 0.037% KCl, 0.0135% Na$_2$HPO$_4$.2H$_2$O, 0.1% Glucan, 0.5% HEPES, pH=7.0) at a concentration of 0.3 μg/μL. To each well of a 384-well plate was added 10 μL of monoamine oxidase B solution, and the test compound with different concentrations (the final concentration of DMSO was 1%) (10 gradient concentrations were 10 mM, 1 mM, 100 μM, 10 μM, 1 μM, 100 nM, 10 nM, 1 nM, 0.1 nM, 0.01 nM) were added into the wells respectively. The standard reference compound was R-(-)-Deprenyl, the plate was incubated at room temperature for 15 min. Then, each well filled with 10 μL substrate solution (Benzylamine hydrochloride, 1 mM) was incubated at room temperature for 60 min. Then 20 μL of fluorescein detection reagent was added to each well, which was fully blended and incubated at room temperature for 20 minutes to produce stable fluorescence signal. The fluorescence signal was read by fluorescein labeling instrument, and the value was expressed by relative light intensity (RLU). The inhibitory rate on enzyme activity was calculated according to the experimental results, the calculated formula: Inh %=(Max−Signal)/(Max−Min)*100, wherein Max was the detected value at the maximum concentration of the sample, Min was the detected value at the minimum concentration of the sample, and Signal was the detected value at the current concentration of the sample.

The standard curve was obtained through the series concentration by experimental test to calculate the IC$_{50}$. The results were shown in Table A1.

TABLE A1 test results of the inhibitory effect of the compound of the invention on the activity of monoamine oxidase B

| Example No. | IC$_{50}$ (μM) |
| --- | --- |
| Example 1 | 0.019 |
| Example 3 | 0.030 |
| Example 8 | 1.4 |
| Example 10 | 1.1 |
| Example 11 | 2.2 |
| Example 12 | 0.72 |
| Example 14 | 0.083 |
| Example 15 | 0.13 |

The test results indicated that the compound of the invention have good inhibitory effects on the activity of monoamine oxidase B.

Example A2: Evaluation of the Inhibitory Effect of the Compound of the Invention on the Activity of Monoamine Oxidase A Test Method:

Human recombinant monoamine oxidase A expressed in Sf9 cells was used in the test system. In the experiment, firstly, the recombinant monoamine oxidase A was dissolved in the pre-configured HEPES buffer (0.8% NaCl, 0.037% KCl, 0.0135% $Na_2HPO_4.2H_2O$, 0.1% Glucan, 0.5% HEPES, pH=7.0) at a concentration of 0.3 μg/μL. To each well of a 384-well plate was added 10 μL of monoamine oxidase A solution, and the test compound with different concentrations (the final concentration of DMSO was 1%) (10 gradient concentrations were 10 mM, 1 mM, 100 μM, 10 μM, 1 μM, 100 nM, 10 nM, 1 nM, 0.1 nM, 0.01 nM) were added into the wells, respectively. The standard reference compound was Clorgyline, the plate was incubated at room temperature for 15 min. Then, each well filled with 10 substrate solution (p-Tyramine hydrochloride, 1 mM) was incubated at room temperature for 60 min. Then 20 μL of fluorescein detection reagent was added to each well, which was fully blended and incubated at room temperature for 20 minutes to produce stable fluorescence signal. The fluorescence signal was read by fluorescein labeling instrument, and the value was expressed by relative light intensity (RLU). The inhibitory rate on enzyme activity was calculated according to the experimental results, the calculated formula: Inh %=(Max−Signal)/(Max−Min)*100, wherein Max was the detected value at the maximum concentration of the sample, Min was the detected value at the minimum concentration of the sample, and Signal was the detected value at the current concentration of the sample.

The standard curve was obtained through the series concentration by experimental test to calculate the $IC_{50}$. The results were shown in Table A2.

TABLE A2 test results of the inhibitory effect of the compound of the invention on the activity of monoamine oxidase A

| Example No. | $IC_{50}$ (μM) |
| --- | --- |
| Example 1 | 46 |
| Example 3 | 29 |
| Example 14 | 27 |
| Example 15 | 29 |

The test results indicated that the compound of the invention have inhibitory effects on the activity of monoamine oxidase A; However, according to data listed in Table A1, the inhibitory effect of the compounds of the present invention on monoamine oxidase B is obviously superior to that on monoamine oxidase A, especially the compounds of embodiments 1, 3, 14 and 15 of the present invention. That is to say, the compound of the invention has selective inhibition on monoamine oxidase B.

Example B: Pharmacokinetic Evaluation after Administering a Certain Amount of the Compound of the Invention by Intravenous or Gavage to Rats, Dogs or Monkeys 1) Animal Subjects:
Rats, dogs or monkeys, specific cases were as shown in Table 1:

TABLE 1

| Germline | Grade | sex | Quantity | Weight | Source |
| --- | --- | --- | --- | --- | --- |
| SD rats | SPF level | male | 6 | 180-220 g | Changzhou Cavens |
| Beagle dogs | Conventional | male | 3 | 5-7 kg | Beijing Marshall |
| Monkeys | Conventional | male | 3 | 5-6 kg | Guangdong Landaubio |

2) Analysis Method:

The LC-MS/MS system comprises Agilent 1200 series vacuum degassing furnace, quaternary pumps, well-plate autosampler, thermostatted column compartment, the API4000Qtrap Triple Quadrupole Mass Spectrometer with an electrospray ionization (ESI) source. Quantitative analysis was carried out using MRM mode. The parameters for MRM transitions are in Table 2.

TABLE 2

| Curtain Gas/CUR | 20 psi |
| --- | --- |
| Nebulizer Gas/GS1 | 550 psi |
| Heater Gas/GS2 | 55 psi |
| Ion transport voltage IS(V)/NC (mA) | 5500 |
| Nebulization temperature/TEM | 550° C. |
| Fragmentor | 30 V |
| Capillary voltage | 140 V |
| Temperature of drying gas | 350° C. |
| Nebulizer | 40 psi |
| Drying gas flow rate | 9 L/min |

Analysis was carried out on waters xbridge C18 (2.1×50 mm, 3.5 μM column, 0.5 μL of sample), the analytic conditions are mobile phases cosisting of water+2 mM ammonium formate+0.1% formic acid (Phase A) and methanol+2 mM ammonium formate+0.1% formic acid (Phase B). The flow rate was 0.4 mL/min. And the gradient of Mobile phase was in Table 3.

TABLE 3

| Time | Gradient of Mobile Phase B |
| --- | --- |
| 0.5 min | 20% |
| 1.2 min | 90% |
| 2.7 min | 90% |
| 2.81 min | 20% |
| 4.0 min | stop |

3) Test Method:

The pharmacokinetic evaluation of the compound in rats, dogs and monkeys was carried out. The specific steps were as follows:

Each animal species was divided into two groups: one was administered intravenously and the other was administered intragastrically. The compounds disclosed herein were administered in form of a solution containing 5% DMSO+ 5% Kolliphor HS15+90% Saline. For the group of intravenous administration, the administration dose was 1 mg/kg, and vein blood samples (0.3 ml) were collected at the time points of 0.083, 0.25, 0.5, 1.0, 2.0, 4.0, 6.0, 8.0 and 24 h after drug administration, then plasma solutions were collected by centrifuging each blood sample at 3000 rpm or 4000 rpm for 10 minutes and kept at −20° C. or −70° C. For the group of intragastric administration, the administration dose was 5 mg/kg, and vein blood samples (0.3 mL) were collected at the time points of 0.25, 0.5, 1.0, 2.0, 4.0, 6.0, 8.0 and 24 h after drug administration, then plasma solutions were collected by centrifuging each blood sample at 3000 rpm or 4000 rpm for 10 minutes and kept at −20° C. or −70° C.

20 μL of plasma was blended with 120 μl, 50 ng/ml propranolol standard water solution, then the mixture was extracted with 1.0 mL methyl tert-butyl ether (MTBE), 0.7 mL of supernatant was dried by blow with nitrogen and then dissolved again with 220 μL methanol water (methanol/water (v/v)=1/1). LC-MS/MS method was used to detect the concentration of the target compounds, and non-atrioventricular model was used to calculate the pharmacokinetic parameters.

The results showed that the compounds administered intravenously and intragastrically in rats, dogs and monkeys had good pharmacokinetic properties, such as high exposure level, low clearance and high bioavailability, and the like. It indicates that the compound of the invention has better drug properties and better clinical application prospect. Wherein the pharmacokinetic parameters of examples 1, 3 and 12 in rats were detailed in Table B1; the pharmacokinetic parameters of examples 1 and 3 in dogs were detailed in Table B2; and the pharmacokinetic parameters of example 1 and 3 in monkeys were detailed in Table B3.

TABLE B1

Pharmacokinetic parameters of examples 1, 3 and 12 in rats

| Example No. | Example 1 | | Example 3 | | Example 12 | |
|---|---|---|---|---|---|---|
| Groups | i.v group | i.g group | i.v group | i.g group | i.v group | i.g group |
| Dose (mg/kg) | 1 | 5 | 1 | 5 | 1 | 5 |
| $T_{max}$ (h) | 0.083 | 0.333 | 0.083 | 0.625 | 0.083 | 0.333 |
| $C_{max}$ (ng/mL) | 690 | 1000 | 681 | 700 | 661 | 1010 |
| $AUC_{last}$ (h*ng/mL) | 505 | 1400 | 582 | 1520 | 452 | 1820 |
| $AUC_{INF}$ (h*ng/mL) | 507 | 1400 | 582 | 1550 | 453 | 1830 |
| $MRT_{INF}$ (h) | 0.694 | 1.08 | 0.778 | 2.11 | 0.666 | 1.31 |
| $T_{1/2}$ (h) | 0.67 | 0.565 | 0.712 | 1.23 | 0.617 | 0.652 |
| F (%) | — | 55.2 | — | 53.3 | — | 80.7 |
| Cl (mL/min/kg) | 32.9 | — | 28.7 | — | 36.8 | — |

TABLE B2

Pharmacokinetic parameters of examples 1 and 3 in dogs

| | Example 1 | | Example 3 | |
|---|---|---|---|---|
| Groups | i.v group | i.g group | i.v group | i.g group |
| Dose(mg/kg) | 1 | 5 | 1 | 5 |
| $T_{max}$(h) | 0.083 | 0.833 | 0.083 | 0.5 |
| $C_{max}$(ng/ml) | 1230 | 1730 | 1490 | 1380 |
| $AUC_{last}$(h*ng/mL) | 1480 | 4930 | 977 | 2440 |
| $AUC_{INF}$(h*ng/mL) | 1500 | 4990 | 979 | 2450 |
| $MRT_{INF}$(h) | 2.77 | 2.98 | 0.871 | 1.44 |
| $T_{1/2}$(h) | 5.05 | 3.27 | 1.13 | 1.09 |
| F(%) | — | 66.5 | — | 50.1 |
| Cl(mL/min/kg) | 11.1 | — | 17 | — |

TABLE B3

Pharmacokinetic parameters of examples 1 and 3 in monkeys

| | Example 1 | | Example 3 | |
|---|---|---|---|---|
| Groups | i.v group | i.g group | i.v group | i.g group |
| Dose(mg/kg) | 1 | 5 | 1 | 5 |
| $T_{max}$(h) | 0.083 | 1 | 0.083 | 1 |
| $C_{max}$(ng/mL) | 924 | 2280 | 1610 | 2010 |
| $AUC_{last}$(h*ng/mL) | 2120 | 11300 | 3240 | 11200 |
| $AUC_{INF}$(h*ng/mL) | 2210 | 11400 | 3260 | 11200 |
| $MRT_{INF}$(h) | 2.35 | 4.33 | 3.41 | 5.02 |
| $T_{1/2}$(h) | 1.77 | 2.8 | 2.24 | 3.39 |
| F(%) | — | 107.1 | — | 69.1 |
| Cl(mL/min/kg) | 7.54 | — | 5.12 | — |

The assay results show that the compounds of the invention have good pharmacokinetic properties in rats, dogs and monkeys.

Example C: Evaluation of Blood-Brain Barrier (BBB) after Peritoneal Injection of the Compound of the Invention in Rats 1) Animal Subjects:

SD rats, specific cases were as shown in Table 4:

TABLE 4

| Germline | Grade | sex | Quantity | Weight | Source |
|---|---|---|---|---|---|
| SD rats | SPF level | male | 18 | 180-220 g | Hunan SJA |

2) Analysis Method:

The analysis method was the same as example B.

3) Test Method:

The experiment was divided into three groups: 15 min group, 1 h group and 2 h group. After overnight fasting for 12 hours, SD rats were administered by intraperitoneal injection with the compound of the invention in the form of 5% DMSO+5% Kolliphor HS15+90% Saline solution at a dose of 10 mg/kg. Blood, cerebrospinal fluid and brain tissue were collected at 15 minutes, 1 hour and 2 hours respectively after administration. Blood samples were centrifuged at 3,000 or 4,000 rpm for 10 minutes. The plasma solution was collected and kept at −20° C. or −70° C. The cerebrospinal fluid was processed using a protein precipitation method. A certain volume of cerebrospinal fluid sample were precisely absorbed and precipitated by adding 5 times acetonitrile solution containing internal standard. The mixture was mixed well by vortexing, and then centrifuged for 2 minutes at 12,000 rpm at 4° C., the supernatant was kept at −80° C. Brain tissue was homogenized with 2 times methanol solution, and centrifuged to get the supernatant, the supernatant were precipitated by adding 5 times acetonitrile solution containing internal standard.

The mixture was mixed well by vortexing, and then centrifuged for 2 minutes at 12,000 rpm at 4° C., the supernatant was kept at −80° C. LC-MS/MS method was used to detect the concentration of target compounds, BBB permeability was calculated and statistical analysis was carried out.

The analysis results showed that the compound of the invention has obvious distribution in brain tissue after intraperitoneal injection, and the ratio of brain tissue to plasma (T/P Ratio) is greater than 1, it is the highest at 1 hour, which showed that the compound of the invention is easy to penetrate the blood-brain barrier after intraperitoneal injection, and the compound in brain tissue has a higher concentration. Wherein the concentrations of example 1 and 3 at 15 min, 1 h and 2 h in plasma, cerebrospinal fluid and brain tissue and T/P Ratio were detailed in Table C.

Table C the concentrations and T/P Ratio of example 1 and 3 at 15 min, 1 h and 2 h in plasma, cerebrospinal fluid and brain tissue

| Example 1 | | | |
|---|---|---|---|
| Time (min) | Plasm (plasma) | CSF (cerebrospinal fluid) | Brain (brain tissue) |
| | Conc. (ng/g or ng/ml) | | |
| 15 | 5203.33 | 147.67 | 10243.33 |
| 60 | 2073.33 | 61.9 | 9273.33 |
| 120 | 864.33 | 34.4 | 2890 |
| | T/P Ratio | | |
| 15 | 1 | 0.028 | 1.969 |
| 60 | 1 | 0.030 | 4.473 |
| 120 | 1 | 0.040 | 3.344 |

| Example 3 | | | |
|---|---|---|---|
| Time (min) | Plasm (plasma) | CSF (cerebrospinal fluid) | Brain (brain tissue) |
| | Conc. (ng/g or ng/ml) | | |
| 15 | 3496.67 | 56.67 | 8610 |
| 60 | 1930 | 39.77 | 5253.33 |
| 120 | 686.67 | 13.05 | 1576.67 |
| | T/P Ratio | | |
| 15 | 1 | 0.016 | 2.462 |
| 60 | 1 | 0.021 | 2.722 |
| 120 | 1 | 0.019 | 2.296 |

Example D: Inhibitory Effect of Compounds of the Invention on Potassium Channel of hERG Detected by Electrophysiological Manual Patch Clamp 1) Test System:

The cell line was derived from HEK-293 cells overexpressed potassium channel of hERG.

The cells were cultured in a 5% $CO_2$ incubator at 37° C. When the cell density reached 80% of the culture dish, the cells were pre-cleaned with phosphate buffer (PBS), and then digested with trypsin/EDTA for 2-3 minutes. and then the cell culture medium was added to stop digestion. The cells were blew with a pipette gently and transferred to a centrifugal tube. The cells were centrifuged for 3 minutes at 1,000 rpm. The supernatant was poured out. The cell culture medium was added and blew gently to mix the cells well. Then the cells were transferred to a culture dish for subculture, or the cells were dropped onto a circular slide and placed in a culture dish until cell adherence for experiment.

Cell culture medium comprises DMEM (Dulbecco's modified Eagle medium), 15% fetal bovine serum and 1% 100× penicillin-streptomycin.

2) Test Method:

Steady cells were dripped onto a circular slide and placed in a Petri dish. The cell density was less than 50% and cultured overnight. The cells for experimental were transferred to a bathtub about 1 ml embedded in an inverted microscope platform, and the extracellular fluid was perfused at a perfusion rate of 2.7 ml/min. The experiment could begin after 5 minutes of stabilization. HEKA EPC-10 patch clamp amplifier and PATCH MASTER acquisition system were used to record membrane current (HEKA Instruments Inc., D-67466 Lambrecht, Pfalz, Germany). All the experiments were performed at room temperature (22-24° C.). In the experiment, the P-97 microelectrode drawing instrument (Sutter Instrument Company, OneDigital Drive, Novato, Calif. 94949) was used to straighten the electrode (BF150-110-10). The inner diameter of the electrode was 1-1.5 mm, and the water-entry resistance was 2-4 M after filling the inner liquid.

The electrophysiological stimulation process of hERG potassium channel comprises clamping the membrane voltage at −80 mV firstly, giving cells 2 seconds and +20 mV voltage stimulation, activating hERG potassium channel, then repolarizing to −50 mV lasting 5 seconds, and generating outward tail current, the stimulus frequency is one time every 15 seconds. The current value is the peak value of the tail current.

hERG potassium channel current was recorded by using the whole cell recording mode. Firstly, the extracellular fluid (about 2 milliliters per minute) was perfused and recorded continuously, and waiting the current stabilization (Run-Down was less than 5% in 5 minutes). At this time, the peak value of tail current was the control current value. Then the extracellular fluid containing the tested compounds was perfused (the concentration of the tested compounds were 0.37 μM, 1.10 μM, 3.30 μM, 10.00 μM and 30.00 μM, respectively) and current value was recorded continuously until the inhibitory effect of the tested compounds on hERG current reached a stable state. At this time, the peak value of tail current was the current value after adding the tested compounds. The stable state was judged by the coincidence of the nearest three continuous current recording lines. After reaching a stable state, if the hERG current after irrigating with extracellular fluid returns to or approaches the value before adding the test compound, the other concentration or other test compounds can be continuously tested by perfusion. 30 μM Quinidine was used as a standard reference compound in the experiment to ensure that the used cells responded normally. In this experiment, the maximum current values of the control group and the test compound group were measured, the ratio of the maximum current value of the test compound group to the maximum current value of the control group was calculated, and the inhibitory effect of the test compound on the potassium channel of hERG (Mean+SE) at the test concentration was evaluated.

3) Data Analysis and Statistics:

The experimental data were collected by PATCHMASTER V2X60 (HEKA Instruments Inc., D-67466 Lambrecht, Pfalz, Germany), and analyzed statistically by using Origin 8.5 (OriginLab Corporation, Northampton, Mass.) software and Microsoft Excel.

The experimental results showed that the compounds of the invention have almost no inhibitory effect on the potassium channel of hERG in the range of test concentration ($IC_{50}$>30 μM), indicating that the compounds of the invention have almost no cardiac risk caused by the action on the potassium channel of hERG. The example 1 has $IC_{50}$>30 μM acting on hERG potassium channel.

Reference throughout this specification to "an embodiment", "some embodiments", "one embodiment", "another example", "an example", "a specific example" or "some examples" means that a particular feature, structure, material, or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific example" or "in some examples," in various places throughout this specification are not necessarily referring to the same embodiment or example of the present disclosure. Furthermore, the particular features, structures, materials, or characteristics may be combined in any suitable manner in one or more embodiments or examples as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having Formula (I) or a stereoisomer, a geometric isomer, a tautomer, an N-oxide, a hydrate, a solvate, a metabolite, a pharmaceutically acceptable salt or a prodrug thereof,

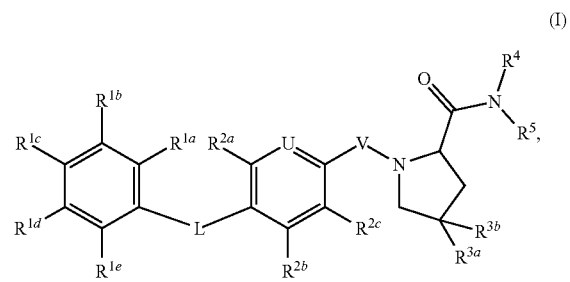

wherein

L is —$CH_2O$— or —$OCH_2$—;

U is $CR^u$ or N;

V is —$CH_2$—, —$CH_2CH_2$— or a single bond;

each $R^{1a}$, $R^{1b}$, $R^{1c}$, $R^{1d}$ and $R^{1e}$ is independently H, D, F, Cl, Br, I, —CN, —$NO_2$, —$NH_2$, —OH, —SH, —COOH, —C(=O)$NH_2$, —C(=O)$NHCH_3$, —C(=O)N($CH_3$)$_2$, —C(=O)—($C_1$-$C_6$ alkyl), —C(=O)—($C_1$-$C_6$ alkoxy), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylamino, hydroxy-substituted $C_1$-$C_6$ alkyl, $C_3$-$C_8$ cycloalkyl, 3-8 membered heterocyclyl, $C_6$-$C_{10}$ aryl or 5-10 membered heteroaryl;

$R^u$ is H, D, F, Cl, Br, I, —CN, —$NO_2$, —$NH_2$, —OH, —SH, —COOH, —C(=O)$NH_2$, —C(=O)$NHCH_3$, —C(=O)N($CH_3$)$_2$, —C(=O)—($C_1$-$C_6$ alkyl), —C(=O)—($C_1$-$C_6$ alkoxy), $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylamino, hydroxy-substituted $C_1$-$C_6$ alkyl, $C_3$-$C_8$ cycloalkyl, 3-8 membered heterocyclyl, $C_6$-$C_{10}$ aryl or 5-10 membered heteroaryl;

each $R^{2a}$, $R^{2b}$ and $R^{2c}$ is independently H, D, F, Cl, Br, I, —CN, —$NO_2$, —$NH_2$, —OH, —SH, —COOH, —C(=O)$NH_2$, —C(=O)$NHCH_3$, —C(=O)N($CH_3$)$_2$, —C(=O)—($C_1$-$C_6$ alkyl), —C(=O)—($C_1$-$C_6$ alkoxy), $C_1$-$C_6$ alkyl, $C_2$-$C_6$ alkenyl, $C_2$-$C_6$alkynyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylamino, hydroxy-substituted $C_1$-$C_6$ alkyl, $C_3$-$C_8$ cycloalkyl, 3-8 membered heterocyclyl, $C_6$-$C_{10}$ aryl or 5-10 membered heteroaryl;

$R^{3a}$ is F, Cl, Br, I, $C_1$-$C_6$ alkyl, $C_1$-$C_6$ haloalkyl, $C_2$-$C_6$ alkoxy, $C_1$-$C_6$ haloalkoxy or hydroxy-substituted $C_1$-$C_6$alkyl;

$R^{3b}$ is H, D, F, Cl, Br, I, $C_1$-$C_6$ alkyl, $C_1$-$C_6$ haloalkyl, $C_1$-$C_6$ alkoxy, $C_1$-$C_6$ haloalkoxy or hydroxy-substituted $C_1$-$C_6$alkyl; and each $R^4$ and $R^5$ is independently H, D, $C_1$-$C_6$alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylamino, hydroxy-substituted $C_1$-$C_6$ alkyl, $C_3$-$C_8$ cycloalkyl, 3-8 membered heterocyclyl, $C_6$-$C_{10}$ aryl or 5-10 membered heteroaryl, wherein each of the $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ alkylamino, hydroxy-substituted $C_1$-$C_6$alkyl, $C_3$-$C_8$ cycloalkyl, 3-8 membered heterocyclyl, $C_6$-$C_{10}$ aryl and 5-10 membered heteroaryl is independently and optionally substituted with 1, 2, 3, 4 or 5 substituents selected from D, F, Cl, Br, I, —OH, —$NH_2$, —$NO_2$, —CN, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl or $C_6$-$C_{10}$ aryl.

2. The compound of claim 1, wherein each $R^{1a}$, $R^{1b}$, $R^{1c}$, $R^{1d}$ and $R^{1e}$ is independently H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—(C$_1$-C$_4$ alkyl), —C(=O)—(C$_1$-C$_4$ alkoxy), C$_1$-C$_4$ alkyl, C$_2$-C$_4$ alkenyl, C$_2$-C$_4$ alkynyl, C$_1$-C$_4$ haloalkyl, C$_1$-C$_4$ alkoxy, C$_1$-C$_4$ haloalkoxy, C$_1$-C$_4$ alkylthio, C$_1$-C$_4$ alkylamino, hydroxy-substituted C$_1$-C$_4$ alkyl, C$_3$-C$_6$cycloalkyl, 3-6 membered heterocyclyl, C$_6$-C$_{10}$ aryl or 5-10 membered heteroaryl;

$R^u$ is H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—(C$_1$-C$_4$ alkyl), —C(=O)—(C$_1$-C$_4$ alkoxy), C$_1$-C$_4$ alkyl, C$_2$-C$_4$ alkenyl, C$_2$-C$_4$ alkynyl, C$_1$-C$_4$ haloalkyl, C$_1$-C$_4$ alkoxy, C$_1$-C$_4$ haloalkoxy, C$_1$-C$_4$ alkylthio, C$_1$-C$_4$ alkylamino, hydroxy-substituted C$_1$-C$_4$ alkyl, C$_3$-C$_6$cycloalkyl, 3-6 membered heterocyclyl, C$_6$-C$_{10}$ aryl or 5-10 membered heteroaryl;

each $R^{2a}$, $R^{2b}$ and $R^{2c}$ is independently H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—(C$_1$-C$_4$ alkyl), —C(=O)—(C$_1$-C$_4$ alkoxy), C$_1$-C$_4$ alkyl, C$_2$-C$_4$ alkenyl, C$_2$-C$_4$alkynyl, C$_1$-C$_4$ haloalkyl, C$_1$-C$_4$ alkoxy, C$_1$-C$_4$ haloalkoxy, C$_1$-C$_4$ alkylthio, C$_1$-C$_4$ alkylamino, hydroxy-substituted C$_1$-C$_4$ alkyl, C$_3$-C$_6$ cycloalkyl, 3-6 membered heterocyclyl, C$_6$-C$_{10}$ aryl or 5-10 membered heteroaryl.

3. The compound of claim 1, wherein each $R^{1a}$, $R^{1b}$, $R^{1c}$, $R^{1d}$ and $R^{1e}$ is independently H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—CH$_3$, —C(=O)—OCH$_3$, methyl, ethyl, n-propyl, i-propyl, allyl, propenyl, propargyl, propinyl, —CHF$_2$, —CF$_3$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofuranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl or quinolyl;

$R^u$ is H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—CH$_3$, —C(=O)—OCH$_3$, methyl, ethyl, n-propyl, i-propyl, allyl, propenyl, propargyl, propinyl, —CHF$_2$, —CF$_3$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofuranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl or quinolyl;

each $R^{2a}$, $R^{2b}$ and $R^{2c}$ is independently H, D, F, Cl, Br, I, —CN, —NO$_2$, —NH$_2$, —OH, —SH, —COOH, —C(=O)NH$_2$, —C(=O)NHCH$_3$, —C(=O)N(CH$_3$)$_2$, —C(=O)—CH$_3$, —C(=O)—OCH$_3$, methyl, ethyl, n-propyl, i-propyl, allyl, propenyl, propargyl, propinyl, —CHF$_2$, —CF$_3$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofuranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl or quinolyl.

4. The compound of claim 1, wherein $R^{3a}$ is F, Cl, Br, I, C$_1$-C$_4$ alkyl, C$_1$-C$_4$ haloalkyl, C$_2$-C$_4$ alkoxy, C$_1$-C$_4$ haloalkoxy or hydroxy-substituted C$_1$-C$_4$ alkyl;

$R^{3b}$ is H, D, F, Cl, Br, I, C$_1$-C$_4$ alkyl, C$_1$-C$_4$ haloalkyl, C$_1$-C$_4$ alkoxy, C$_1$-C$_4$ haloalkoxy or hydroxy-substituted C$_1$-C$_4$alkyl.

5. The compound of claim 1, wherein $R^{3a}$ is F, Cl, Br, I, methyl, ethyl, n-propyl, i-propyl, —CHF$_2$, —CF$_3$, —CHFCH$_2$F, —CF$_2$CHF$_2$, —CH$_2$CF$_3$, —CH$_2$CF$_2$CHF$_2$, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, hydroxymethyl or 2-hydroxyethyl;

$R^{3b}$ is H, D, F, Cl, Br, I, methyl, ethyl, n-propyl, i-propyl, —CHF$_2$, —CF$_3$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, hydroxymethyl or 2-hydroxyethyl.

6. The compound of claim 1, wherein each $R^4$ and $R^5$ is independently H, D, C$_1$-C$_4$alkyl, C$_2$-C$_4$ alkenyl, C$_2$-C$_4$ alkynyl, C$_1$-C$_4$ haloalkyl, C$_1$-C$_4$ alkoxy, C$_1$-C$_4$ haloalkoxy, C$_1$-C$_4$alkylthio, C$_1$-C$_4$ alkylamino, hydroxy-substituted C$_1$-C$_4$alkyl, C$_3$-C$_6$ cycloalkyl, 3-6 membered heterocyclyl, C$_6$-C$_{10}$ aryl or 5-10 membered heteroaryl, wherein each of the C$_1$-C$_4$ alkyl, C$_2$-C$_4$ alkenyl, C$_2$-C$_4$ alkynyl, C$_1$-C$_4$ haloalkyl, C$_1$-C$_4$ alkoxy, C$_1$-C$_4$ haloalkoxy, C$_1$-C$_4$ alkylthio, C$_1$-C$_4$ alkylamino, hydroxy-substituted C$_1$-C$_4$alkyl, C$_3$-C$_6$ cycloalkyl, 3-6 membered heterocyclyl, C$_6$-C$_{10}$ aryl and 5-10 membered heteroaryl is independently and optionally substituted with 1, 2, 3, 4 or 5 substituents selected from D, F, Cl, Br, I, —OH, —NH$_2$, —NO$_2$, —CN, C$_1$-C$_4$ alkyl, C$_1$-C$_4$ haloalkyl, C$_1$-C$_4$ alkoxy, C$_1$-C$_4$ haloalkoxy, C$_3$-C$_6$ cycloalkyl or C$_6$-C$_{10}$ aryl.

7. The compound of claim 1, wherein each $R^4$ and $R^5$ is independently H, D, methyl, ethyl, n-propyl, i-propyl, allyl, propenyl, propargyl, propinyl, —CHF$_2$, —CF$_3$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofuranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl or quinolyl, wherein each of the methyl, ethyl, n-propyl, i-propyl, allyl, propenyl, propargyl, propinyl, —CHF$_2$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCHFCH$_2$F, —OCF$_2$CHF$_2$, —OCH$_2$CF$_3$, —OCH$_2$CF$_2$CHF$_2$, methylthio, ethylthio, methylamino, dimethylamino, ethylamino, hydroxymethyl, 2-hydroxyethyl, cyclopropyl, cyclobutyl, cyclopentyl, cyclohexyl, azetidinyl, pyrrolidinyl, tetrahydrofuranyl, piperidyl, piperazinyl, morpholinyl, phenyl, indenyl, naphthyl, pyrrolyl, pyrazolyl, imidazolyl, triazolyl, tetrazolyl, furanyl, thienyl, thiazolyl, oxazolyl, pyridyl, pyrimidyl, pyrazinyl, pyridazyl, benzimidazolyl, indolyl and quinolyl is independently and optionally substituted with 1, 2, 3, 4 or 5 substituents selected from D, F, Cl, Br, I, —OH, —NH$_2$, —NO$_2$, —CN, methyl, ethyl, n-propyl, i-propyl, —CHF$_2$, —CF$_3$, —CHFCH$_2$F, —CF$_2$CHF$_2$, —CH$_2$CF$_3$, —CH$_2$CF$_2$CHF$_2$, methoxy, ethoxy, n-propoxy, isopropoxy, —OCHF$_2$, —OCF$_3$, —OCHFCH$_2$F, —OCF$_2$CHF$_2$, —OCH$_2$CF$_3$, —OCH$_2$CF$_2$CHF$_2$, cyclopropyl, cyclobutyl, cyclopentyl, cyclohexyl, phenyl, indenyl or naphthyl.

8. The compound of claim 1 having Formula (II), or a stereoisomer, a geometric isomer, a tautomer, an N-oxide, a hydrate, a solvate, a metabolite, a pharmaceutically acceptable salt or a prodrug thereof,

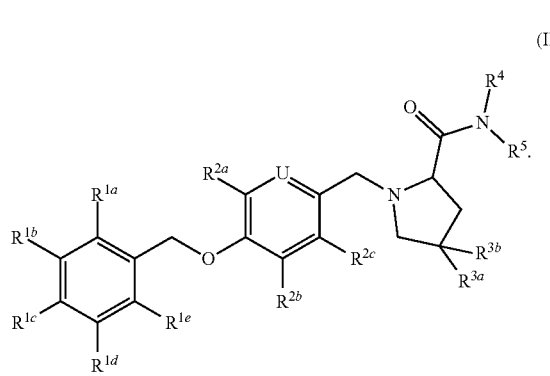

(II)

9. The compound of claim 1 having Formula (III), or a stereoisomer, a geometric isomer, a tautomer, an N-oxide, a hydrate, a solvate, a metabolite, a pharmaceutically acceptable salt or a prodrug thereof,

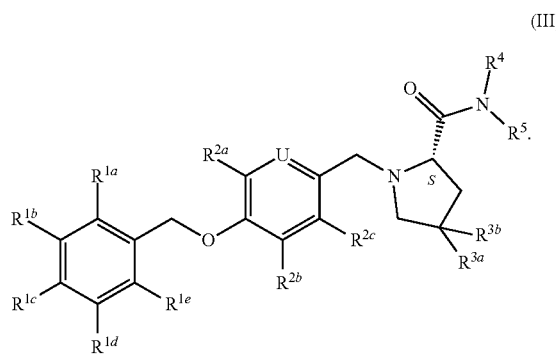

(III)

10. The compound of claim 1 having Formula (IV), or a stereoisomer, a geometric isomer, a tautomer, an N-oxide, a hydrate, a solvate, a metabolite, a pharmaceutically acceptable salt or a prodrug thereof,

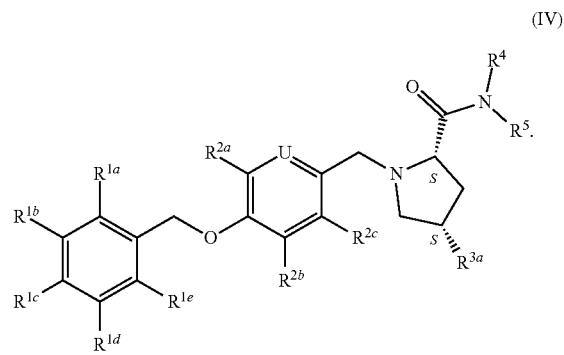

(IV)

11. The compound of claim 1 having Formula (V), or a stereoisomer, a geometric isomer, a tautomer, an N-oxide, a hydrate, a solvate, a metabolite, a pharmaceutically acceptable salt or a prodrug thereof,

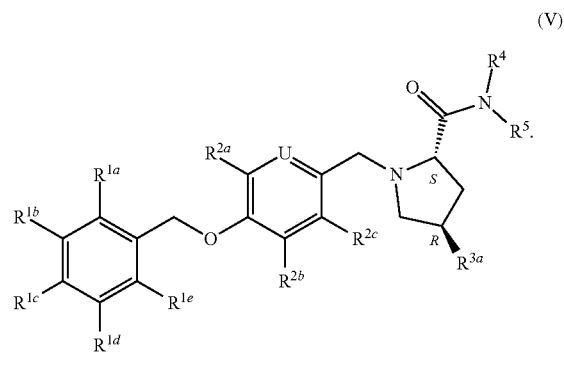

(V)

12. The compound of claim 1 having one of the following structures or a stereoisomer, a geometric isomer, a tautomer, an N-oxide, a hydrate, a solvate, a metabolite, a pharmaceutically acceptable salt or a prodrug thereof:

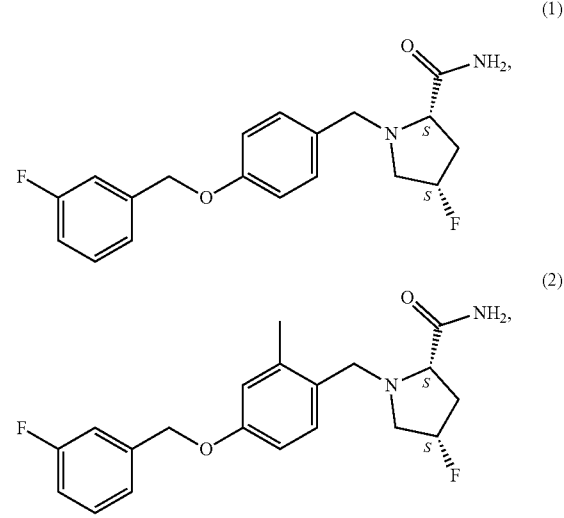

(3)
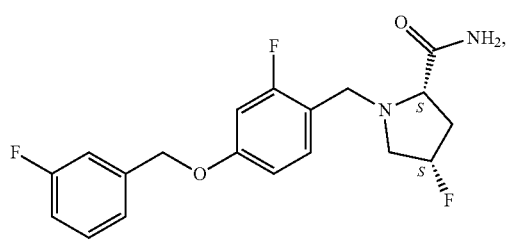
(4)
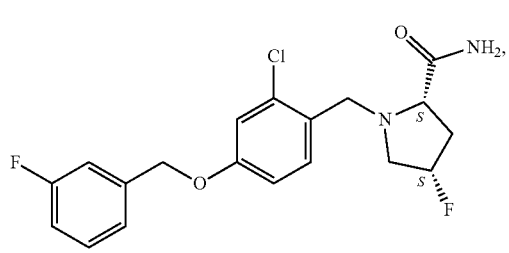
(5)
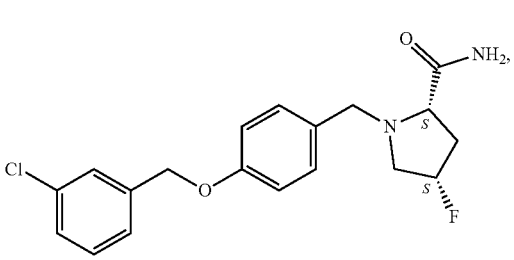
(6)
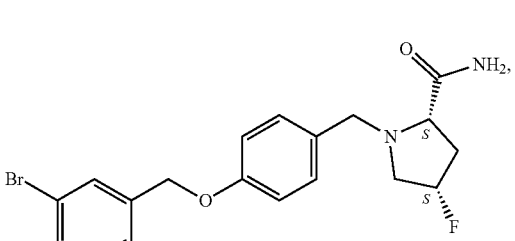
(7)
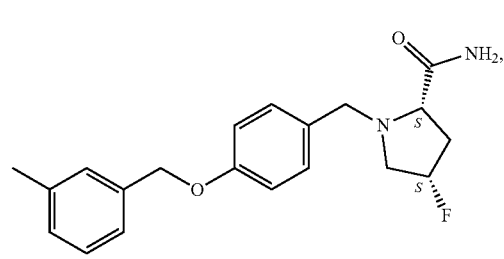
(8)
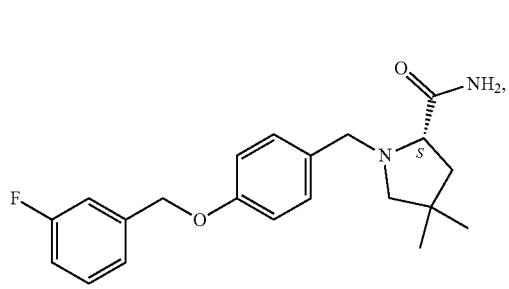
(9)
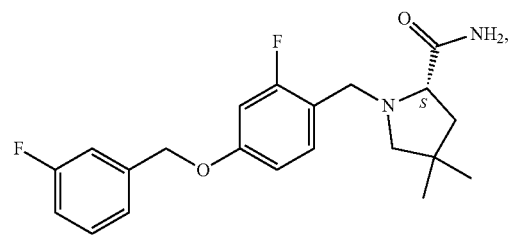
(10)
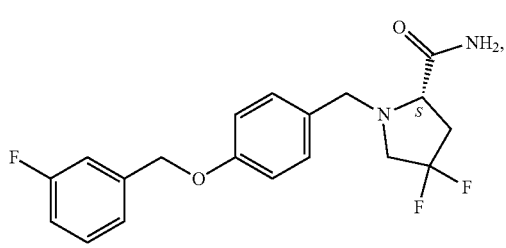
(11)
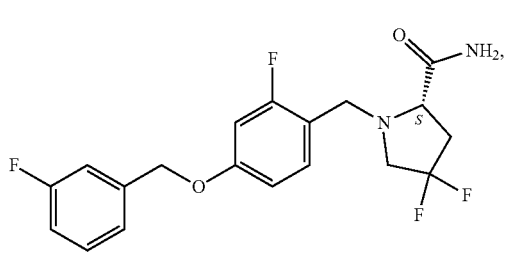
(12)
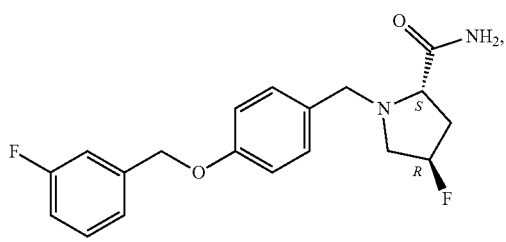
(13)
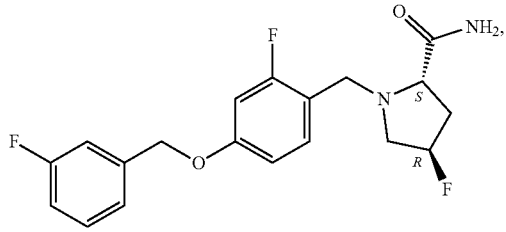
(14)
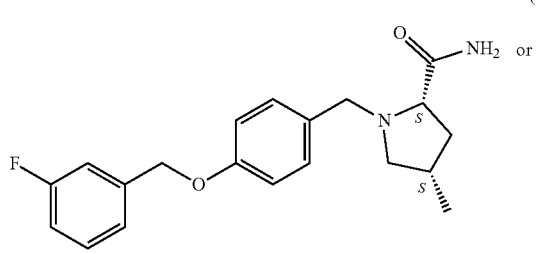

-continued

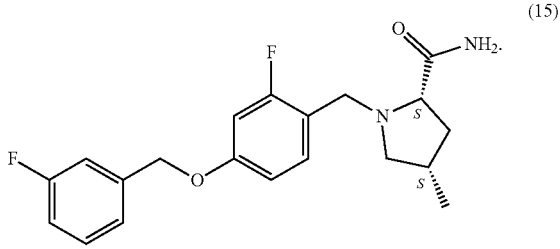

(15)

13. A pharmaceutical composition comprising the compound of claim 1.

14. The pharmaceutical composition according to claim 13, wherein the pharmaceutical composition optionally comprises a pharmaceutically acceptable excipient, carrier, adjuvant or a combination thereof.

15. A method of treating or lessening a disease regulated by MAO-B comprising administering a therapeutically effective amount of the compound of claim 1 to the subject, wherein the disease regulated by MAO-B is a neurodegenerative disease, psychosis or cancer.

16. The method of claim 15, wherein the neurodegenerative disease is Parkinson's disease, cerebral ischemia, Alzheimer's disease, amyotrophic lateral sclerosis, bovine spongiform encephalopathy, Huntington's chorea, Creutzfeldt-Jakob disease, ataxia telangiectasia, cerebellar atrophy, spinal muscular atrophy, primary lateral sclerosis or multiple sclerosis.

17. A method of treating or lessening a disease regulated by MAO-B comprising administering a therapeutically effective amount of the pharmaceutical composition of claim 13 to the subject, wherein the disease regulated by MAO-B is a neurodegenerative disease, psychosis or cancer.

18. The method of claim 17, wherein the neurodegenerative disease is Parkinson's disease, cerebral ischemia, Alzheimer's disease, amyotrophic lateral sclerosis, bovine spongiform encephalopathy, Huntington's chorea, Creutzfeldt-Jakob disease, ataxia telangiectasia, cerebellar atrophy, spinal muscular atrophy, primary lateral sclerosis or multiple sclerosis.

* * * * *